United States Patent
Bertele et al.

(10) Patent No.: US 8,414,820 B2
(45) Date of Patent: Apr. 9, 2013

(54) METHODS FOR ENHANCING AN INTERBODY DEVICE

(75) Inventors: Theodore P. Bertele, Longmont, CO (US); Scott K. Stanley, Parker, CO (US)

(73) Assignee: SB Technologies, LLC, Parker, CO (US)

( * ) Notice: Subject to any disclaimer, the term of this patent is extended or adjusted under 35 U.S.C. 154(b) by 0 days.

(21) Appl. No.: 13/420,221

(22) Filed: Mar. 14, 2012

(65) Prior Publication Data

US 2012/0167367 A1 Jul. 5, 2012

Related U.S. Application Data

(62) Division of application No. 12/697,871, filed on Feb. 1, 2010, now Pat. No. 8,303,879.

(51) Int. Cl.
*B29C 45/16* (2006.01)

(52) U.S. Cl.
USPC .......................................... 264/453; 264/241

(58) Field of Classification Search .................... 264/453
See application file for complete search history.

(56) References Cited

U.S. PATENT DOCUMENTS

| | | | |
|---|---|---|---|
| 6,113,638 A | | 9/2000 | Williams et al. |
| 7,250,060 B2 * | | 7/2007 | Trieu .......................... 623/17.15 |
| 2003/0045939 A1 | | 3/2003 | Casutt |
| 2007/0061015 A1 * | | 3/2007 | Jensen et al. ............... 623/23.51 |
| 2007/0093903 A1 | | 4/2007 | Cheng |
| 2009/0326657 A1 | | 12/2009 | Grinberg et al. |
| 2011/0071635 A1 | | 3/2011 | Zhang et al. |

OTHER PUBLICATIONS

U.S. Appl. No. 13/420,206 Office Action mailed Aug. 3, 2012, 10 pages.
Photographs of admitted prior art, 2 pages, Mar. 14, 2012.
PCT/US11/23376 Search Report and Written Opinion mailed Mar. 25, 2011, 14 pages.
U.S. Appl. No. 12/697,871 Non-Final Office Action mailed Mar. 29, 2012, 10 pages.
U.S. Appl. No. 12/697,871 Response to Office Action filed Jun. 29, 2012, 11 pages.

* cited by examiner

*Primary Examiner* — Monica A Huson
(74) *Attorney, Agent, or Firm* — Lathrop & Gage LLP

(57) ABSTRACT

A composite interbody device includes superior and inferior endplates with a plastic core molded therebetween. The core includes one or more features for permitting bone growth through the core. Each endplate includes a bone interface side coated with hydroxyapatite, for promoting bone on-growth. Pores in the bone interface sides permit bone in-growth. Core interface sides of the endplates include relatively larger pores for accepting molten material from the core, for example during injection molding, to enhance bonding of the endplates with the core. Each endplate has a central barrier layer for preventing the molten core material from extruding through the core interface pores into the bone interface pores, reserving the bone interface pores for bone in-growth. A method of manufacturing the composite interbody device is also disclosed.

14 Claims, 26 Drawing Sheets

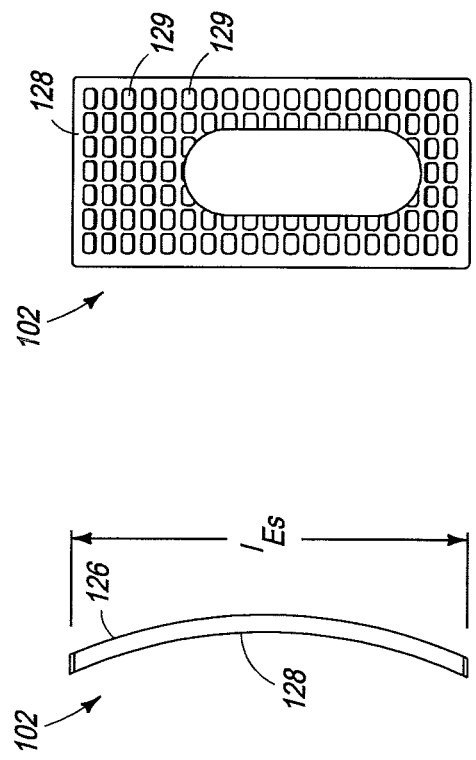
FIG. 7
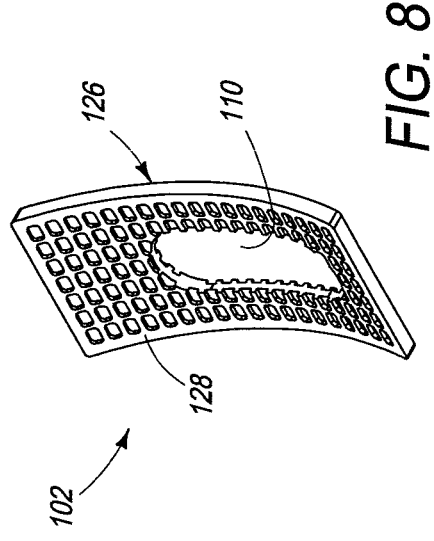
FIG. 8
FIG. 6
FIG. 5

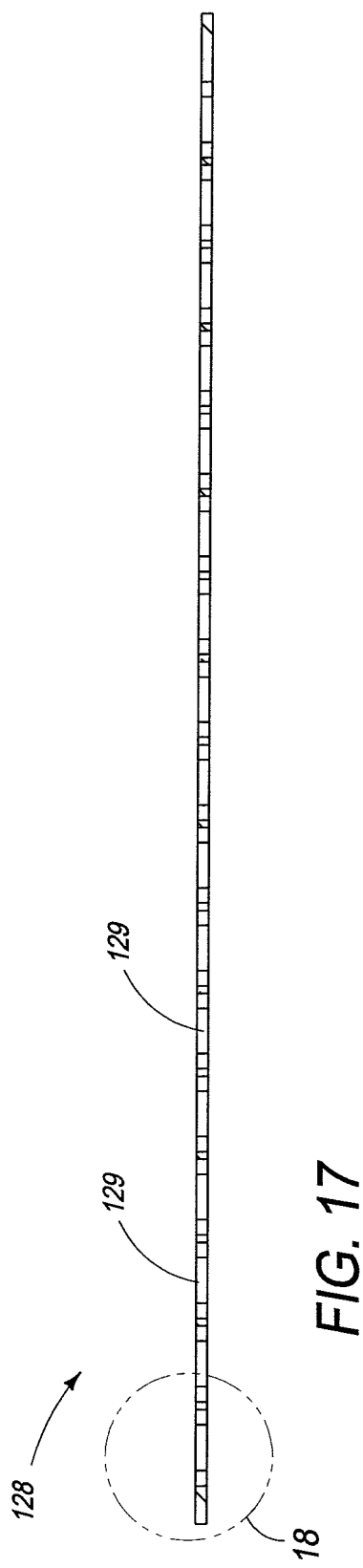
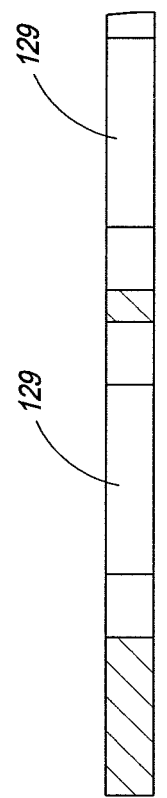
FIG. 17
FIG. 18

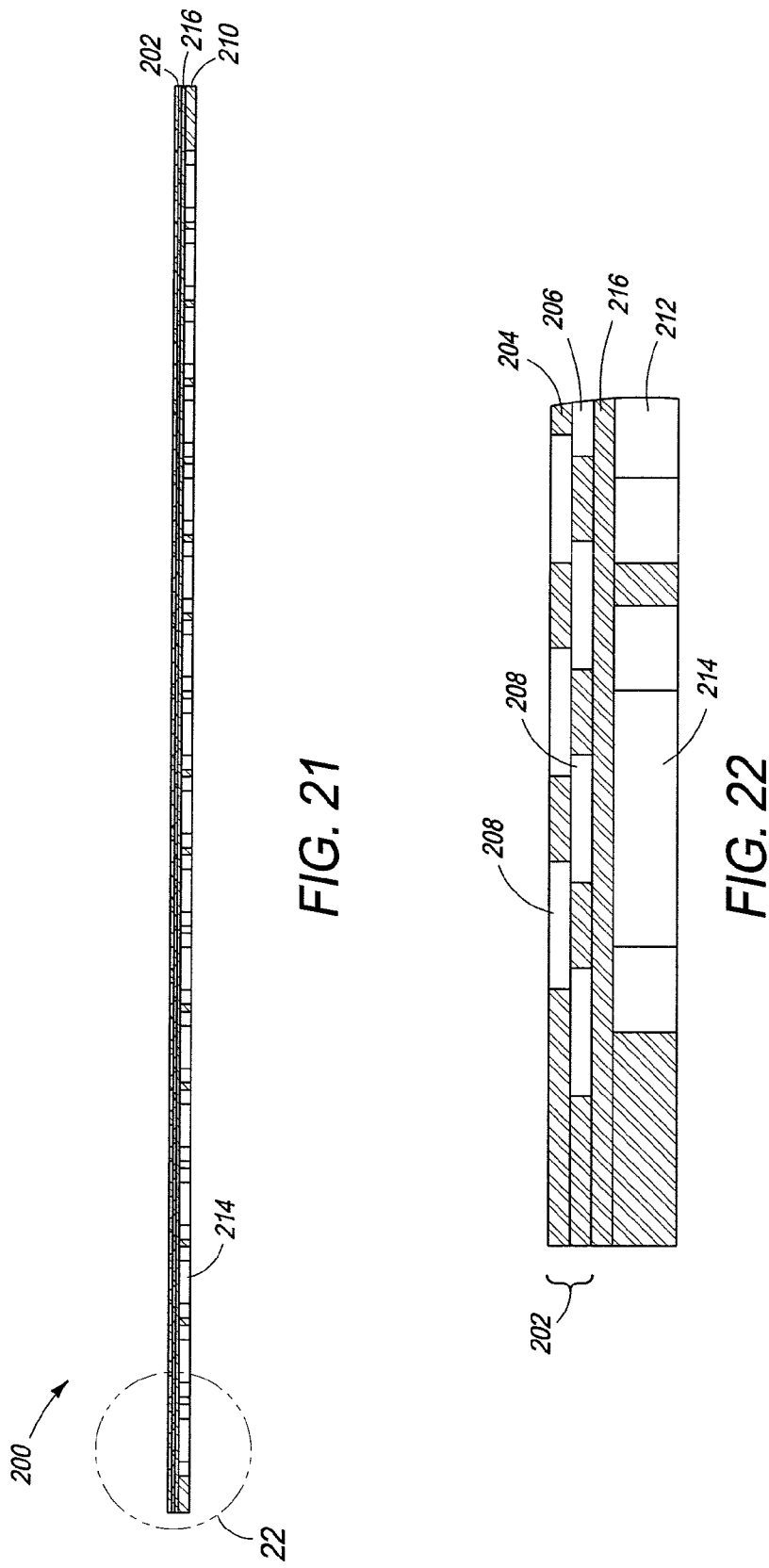

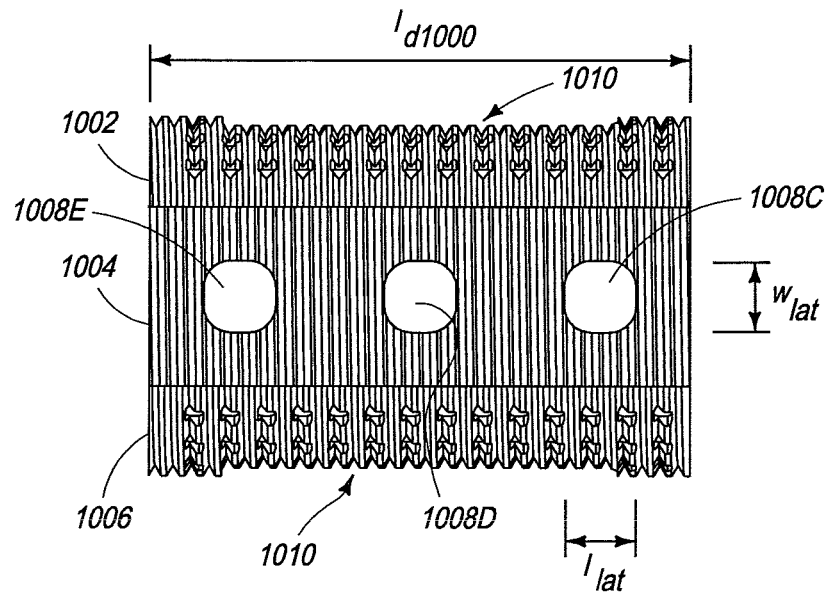
FIG. 42
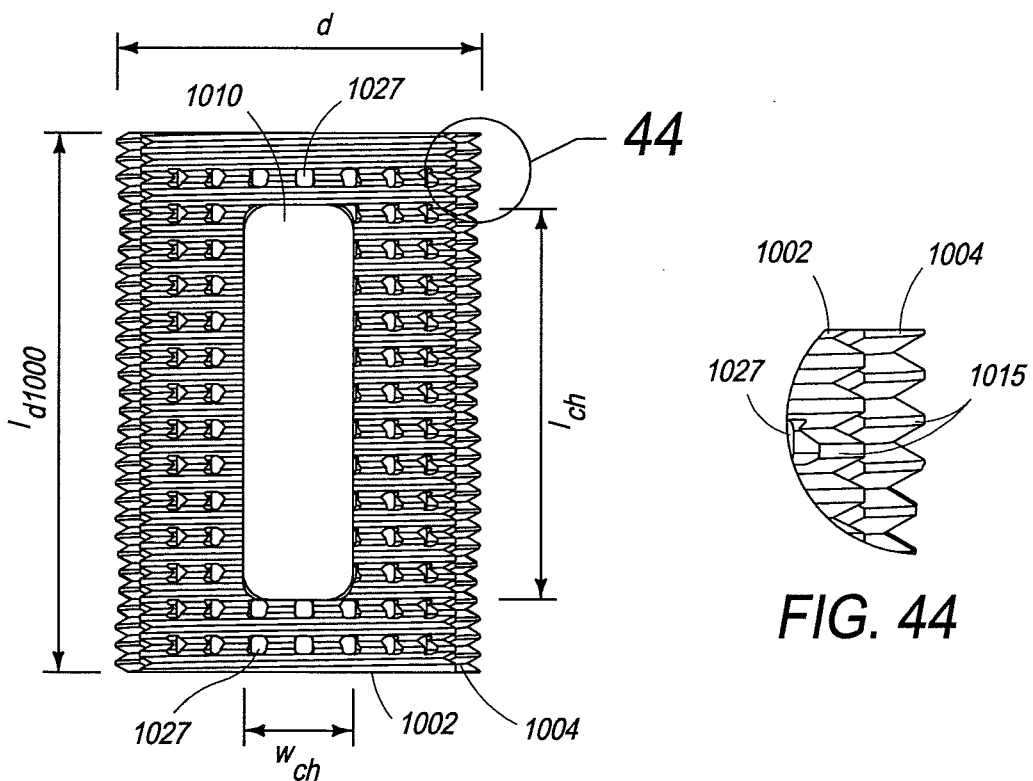
FIG. 43
FIG. 44

METHODS FOR ENHANCING AN INTERBODY DEVICE

RELATED APPLICATIONS

This application is a divisional of U.S. Ser. No. 12/697,871, filed 1 Feb. 2010, now U.S. Pat. No. 8,303,879, and incorporated herein by reference.

BACKGROUND

Spinal fusion treatment is considered a standard of care for intractable lower back pain arising from degenerative disc disease and/or spinal instability. Fusion includes immobilizing the painful spine segments and encouraging bone growth across the immobilized level. In the cervical spine, anterior decompression and fusion is the gold standard.

Spine fusion was first performed without instrumentation using bone grafts, the bone grafts often being obtained from the patient's own body (i.e., from the iliac crest). Instrumented fusion, using rods, plates, and screws, was initially developed to provide rigid stability to the spine while the implanted bone grafts fused across the treated level. Since then, fusion implants have become common, replacing bone grafts.

Conventional implants are designed to facilitate primarily through-growth, or fusion resulting from growth of bone through holes or channels through the implants, for example in order to reach other bone. For example, Medtronic LT Cages® are thimble-like titanium device that are packed with a collagen sponge soaked in rhBMP-2 (recombinant human bone morphogenic protein 2). A pair of the cages are inserted between adjacent vertebrae to initiate bone growth through the cages. Conventional CFR-PEEK cages (carbon fiber reinforced PEEK plastic cages) also rely upon through-growth— for example, the Jaguar™ and Saber™ Lumbar I/F CAGE Systems house autologous cancellous bone grafts that grow through the cages to join with adjacent vertebrae. Alphatec Novel TL spacers are made of PEEK plastic and include an internal chamber allowing for growth of bone therein.

Although effective, through-growth occurs slowly, for example, over a period of a year or more. Through-growth can be further delayed if the implant area is not immobilized. Even micro-motion of the implant area can disturb and disrupt bone growth, leading to increased incidence of subsidence and pseudarthrosis.

Some conventional devices attempt to improve implant stabilization by encouraging bone on-growth—a comparatively rapid, planar growth of bone upon surfaces of an adjacent implant, or upon surfaces of adjacent bone. For example, on-growth may be encouraged by coating a titanium cage with a chemical such as hydroxyapatite, a mineral naturally found in bone, to encourage new-grown bone to stick to the implant surface (for example, as is done with titanium dental implants). However, because they are radio-opaque, titanium cages and implants may hinder diagnostic assessment of bone growth, whether coated with hydroxyapatite or not. For example, implants made primarily of radio-opaque titanium may obscure visualization of bone growth (e.g., through-growth) on x-rays. Titanium may likewise cause signal artifact with MRIs or CTs, making it difficult to determine if fusion has occurred.

In order to avoid the visualization problems of titanium implants, attempts have been made to mix hydroxyapatite with, or apply hydroxyapatite to, radiolucent PEEK plastic (or other non-scattering biocompatible material, e.g., HDPE) to form a cage/implant. However, hydroxyapatite content embrittles the material and weakens such implants. In addition, PEEK provides poorer fixation than titanium, and thus, PEEK implants must often be supplemented with posterior pedicle screw and rod instrumentation.

SUMMARY

The interbody device described herein advances the art of fusion devices by incorporating features to encourage simultaneous on-growth, through-growth and in-growth of bone (in-growth of bone being characterized by bone growing into and around porous implant surface features). Facilitating all three types of bone growth results in faster spinal or other bony fusion. Bony on-growth onto device surfaces provides relatively quick, albeit limited mechanical rigidity. Next, in-growth, as achieved with the device described herein, incrementally increases mechanical strength as bone grows into porous features of the interbody device to anchor bone to the device. Finally, bony through-growth, which takes the longest to complete, fully stabilizes and completes the fusion. On-growth and in-growth enhance device stabilization, thus accelerating complete fusion by minimizing micro-motion that could disrupt through-growth.

The interbody device described herein is primarily discussed in terms of a PEEK plastic core or preexisting interbody device (such as an artificial disc) with metallic endplates. Titanium endplates are discussed in depth; however, it will be appreciated that other biocompatible metals, as well as alternate core or preexisting device materials, may fall within the scope hereof.

In one embodiment, a composite interbody device includes a plastic core with superior and inferior surfaces and one or more features for permitting bone growth through the core. A superior endplate has a core interface side coupled with the superior surface. The superior endplate has a bone interface side opposite the core interface side, for interfacing with bone of an implant site. The bone interface side includes multiple bone interface pores for permitting bone growth therein. A metallic inferior endplate includes a core interface side and a bone interface side opposite the core interface side. The core interface side couples with the inferior surface of the core. The bone interface side interfaces with bone of an implant site and includes bone interface pores for permitting bone growth therein. A hydroxyapatite coating applied to the bone interface sides of the superior and inferior endplates encourages bone growth onto the endplates.

In another embodiment, a composite interbody device includes a superior endplate, an inferior endplate and a core between the superior and inferior endplates. The superior endplate and the inferior end plate each have a hydroxyapatite-coated, porous bone interface side for contacting bone of an implant site. The hydroxyapatite coating encourages bone growth onto the bone interface side, and pores of the bone interface side permit bone growth into the bone interface side. The superior and inferior endplates each have a porous core interface side opposite the bone interface side, a central barrier layer between the core interface side and the bone interface side; and at least one aperture through the endplate. The plastic core has a superior surface bonded with and penetrating pores of the superior endplate core interface side; and an inferior surface bonded with and penetrating pores of the inferior endplate core interface side. At least one channel through the core is aligned with the superior endplate aperture and with the inferior endplate aperture, the channel thus providing a pathway for through growth of bone through the interbody device.

In another embodiment, a composite interbody device has a plastic core with superior and inferior surfaces and one or more features for permitting bone growth through the core. A superior endplate includes a core interface side configured with the superior core surface, and a bone interface side opposite the core interface side, for interfacing with bone of an implant site. The bone interface side is coated with hydroxyapatite and has multiple micro-machined surface features for increasing the bone interface side surface area to enhance bonding between bone and the superior endplate. An inferior endplate has a core interface side configured with the inferior core surface and a bone interface side opposite the core interface side for interfacing with bone of an implant site. The bone interface side is coated with hydroxyapatite and has multiple micro-machined surface features for increasing the bone interface side surface area to enhance bonding between bone and the inferior endplate.

In another embodiment, a method of manufacturing a composite interbody device includes assembling superior and inferior endplates by forming a solid central barrier layer on a bone interface layer, opposite a bone interface side of the bone interface layer. A porous core interface layer is formed on the central barrier layer opposite the bone interface layer. The inferior and superior endplates are placed in a mold, on each side of a core cavity, with the core interface layers facing the core cavity and the bone interface sides facing away from the cavity. Molten plastic is injection-molded into the core cavity, to form a plastic core between the endplates and bonded with core interface sides of the core interface layers. The molten plastic extrudes into pores of the core interface layers to bond with the endplates.

BRIEF DESCRIPTION OF THE DRAWINGS

FIG. 5 is a top view of the superior endplate of FIG. 1, showing a bone interface side.

FIG. 6 is a side view of the superior endplate of FIG. 5.

FIG. 7 is a bottom view of the superior endplate of FIG. 65, showing a core interface side.

FIG. 8 is a perspective view of the superior endplate of FIG. 5.

FIG. 17 is a sectional view through the core interface layer of FIG. 15.

FIG. 18 is an enlargement of a portion of the sectional view of FIG. 17.

FIG. 21 is a sectional view through the endplate of FIGS. 19 and 20.

FIG. 22 is an enlargement of a portion of the sectional view of FIG. 21.

FIG. 42 is a side view of the device of FIG. 40.

FIG. 43 is a top view of the device of FIG. 40, showing additional detail of a superior endplate.

FIG. 44 is an enlarged view of a section of the device shown in FIG. 43.

DETAILED DESCRIPTION

Figure 1:
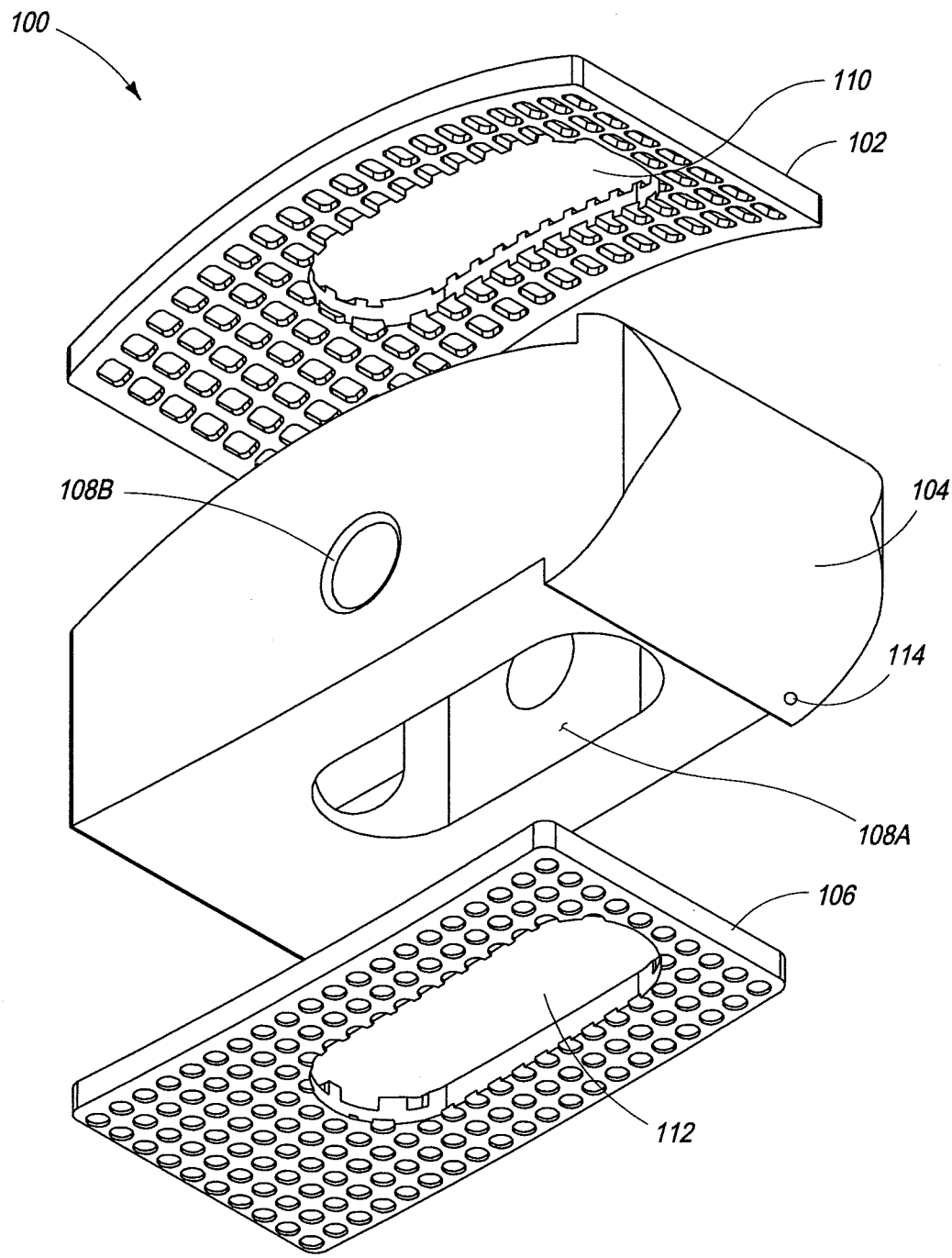
FIG. 1 is a perspective view of a composite interbody device with superior and inferior endplates, according to an embodiment.

FIG. 1 shows a composite interbody device 100 including a superior endplate 102 and an inferior endplate 106, flanking a core 104. Core 104 is for example a PEEK core (i.e., injection molded thermosetting PEEK plastic) having one or more features 108, such as channels through core 104, for encouraging bone growth through device 100, and/or for housing a fusion enhancing material such as bone and any associated growth enhancers, or a fusion enhancing glue. Core 104 may alternately be made of any other biocompatible material that is sufficiently malleable for forming in a desired shape, yet strong enough to meet durability requirements of an intended implant site. Features 108 may be machined after core 104 is injection molded, or features 108 may be extruded or otherwise formed. Feature 108A is a vertically-oriented channel that runs top-to-bottom through core 104, which aligns with an aperture 110 in superior endplate 102 and an aperture 112 through inferior endplate 106, when endplates 102 and 106 are assembled with core 104. Alignment of aperture 110, channel 108A and aperture 112 together form a passage that allows bone growth entirely through device 100. Because PEEK is radiolucent, core 104 may include one or more radio markers 114 for facilitating visualization of core 104 on x-ray during or after implantation.

Feature 108B is a horizontally-oriented aperture or hole in a side of core 102, or alternately, a channel that runs side-to-side through core 104. Feature 108C (labeled in FIG. 2) is a horizontally-oriented aperture or hole in a back side (distal to the spinal cord when inserted between vertebrae) of core 104, or alternately, a channel that runs back-to-front through core 104. In one embodiment, features 108B and 108C open into vertically-oriented channel 108A, thus permitting bone growth through the sides and back of device 100, in addition to vertical bone growth through channel 108 and endplate apertures 110 and 112. Features 108A-C may be created by machining after core 104 is molded (e.g., after injection-molding core 104 between endplates 102 and 106. Alternately, features 108A-C may be molded into device 100 by use of one or more removable mandrels placed in a mold for forming device 100.

As shown, endplates 102/106 are curved to conform to an accepting bony surface, as further described with respect to FIG. 3, below. When core 104 is molded between endplates 102 and 106, device 100 for example assumes a bullet shape that facilitates insertion into an implant site. It will be appreciated that endplates 102 and 106 may be straight, curved, angulated or otherwise shaped, depending upon the intended application (i.e., the intended implant site or intended final shape of device 100). Endplates 102 and 106 are for example diffusion bonded in a press, to achieve a desired shape and/or contour.

Endplates 102/106 are for example porous titanium coated with hydroxyapatite (HA), to encourage both bone on-growth (onto the porous endplates) and in-growth (into pores of the endplates). Coating titanium endplates, rather than a PEEK core directly, with HA promotes bioactivity (e.g., bone growth) without sacrificing strength and toughness of core 104. Titanium is a biocompatible material that bonds with HA and therefore facilitates bone on-growth with endplates 102 and 104. Titanium HA coated endplates provide strength, biocompatibility and on-growth without compromising the strength of the PEEK core as occurs when HA is blended directly into PEEK (PEEK fracture toughness is known to be degraded with direct application of HA). In addition, the titanium-PEEK-titanium combination of device 100 avoids the greater stiffness of a primarily titanium implant, thereby reducing stress shielding that inhibits bone growth and bone fusion. It will be appreciated that other biocompatible metals such as molybdenum, cobalt-chrome, stainless steels and other biocompatible alloys, may be used in place of or in addition to titanium in forming endplates 102 and 106. For example other biocompatible metals may be alloyed with titanium to form endplates 102 and 106.

Figure 2:
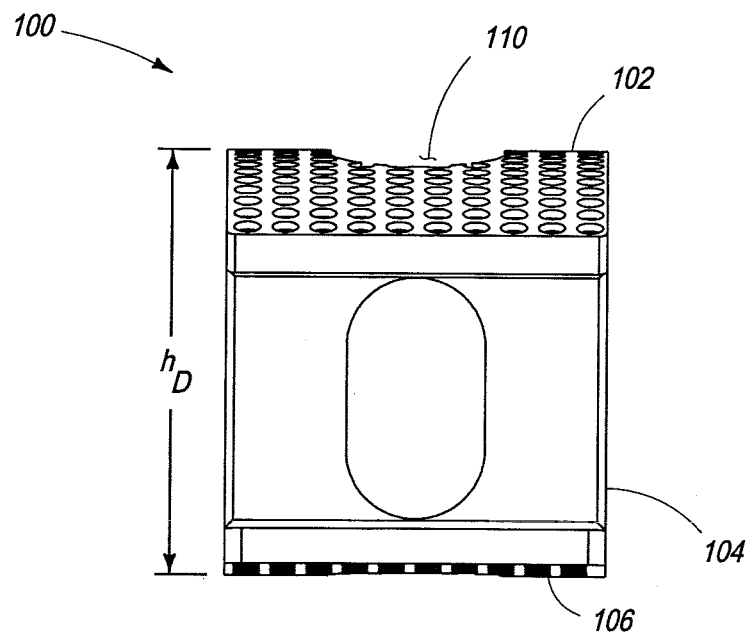
FIG. 2 is a cross-sectional view through the interbody device of FIG. 1.

FIG. 2 is a rear view of device 100, featuring endplates 102 and 106 configured with core 104 and showing rear feature 108C. Rear feature 108C is an aperture in core 104 having dimensions of about 4 mm wide by 3-6 mm high. In addition to permitting bone growth through the back end of core 104, feature 108C facilitates placement of device 100 at an implant site by use of a tool sized to fit feature 108C.

In one aspect, height ($h_D$) of device 100, including endplates 102 and 106, ranges from about 12 mm to about 17.1 mm. When aligned with channel 108A, aperture 110 of superior endplate 102 and aperture 112 of inferior endplate 106 may open into common space within core 104, which is also accessible via at least feature 108C.

Figure 3:
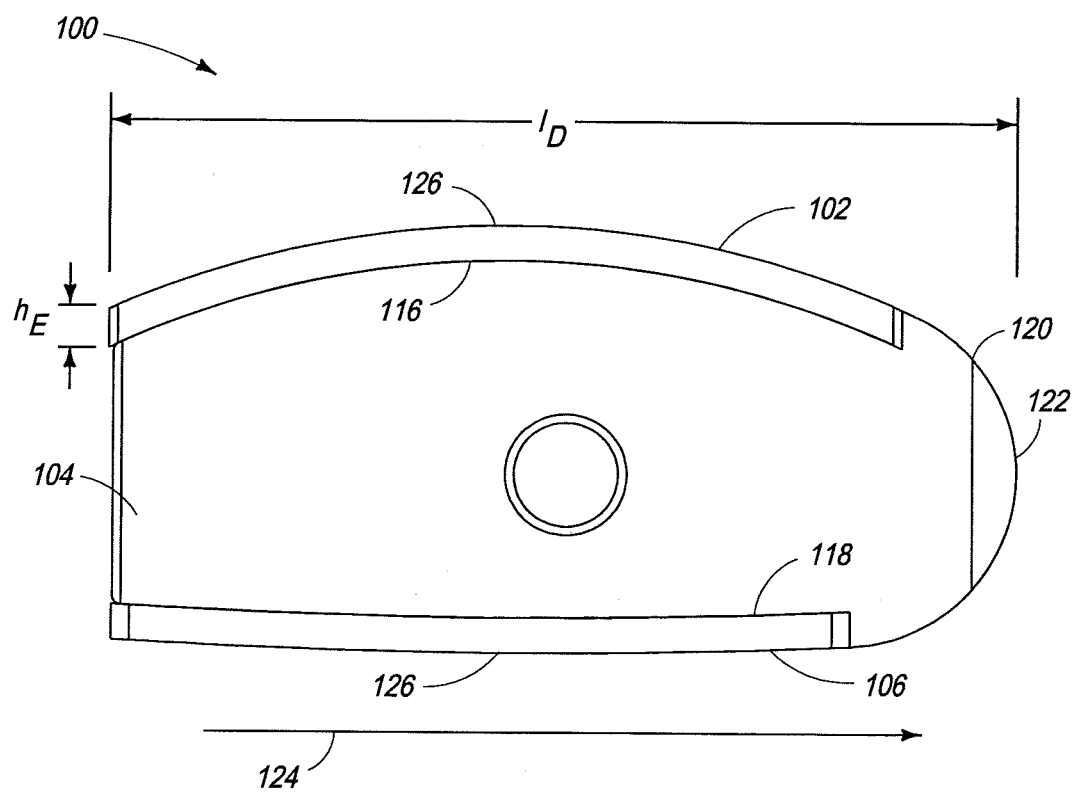
FIG. 3 is a side view of the interbody device of FIG. 1.

FIG. 3 is a side view of assembled device 100. In one aspect, device 100 includes superior and inferior endplate contact surfaces 116 and 118, spanning at least a portion of the length ($l_D$) of device 100/core 104. Length $l_D$ is for example about 26 mm. Endplates 102/106 are curved to conform with a shape of contact surfaces 116 and 118. Although not shown in FIG. 3, it will be appreciated that endplates 102 and 106 may also be shaped on bone interface sides 126, opposite the endplate contact surfaces, to conform or optimally interact with bony surfaces of an intended insertion site. Core 104 may be beveled starting at a bevel line 120 to a nose 122, to facilitate insertion between bony surfaces such as adjacent vertebrae. Device 100 is for example inserted nose-first between vertebrae in the direction indicated by insertion arrow 124. Endplates 102/106 have an endplate height ($h_E$) of between about 1-2 mm. Endplates 102/106 may be coated with hydroxyapatite before or after assembly with core 104. In one example, endplates 102/106 are spray coated with hydroxyapatite prior to placement in a mold, and core 104 is injection molded between endplates 102/106.

Figure 4:
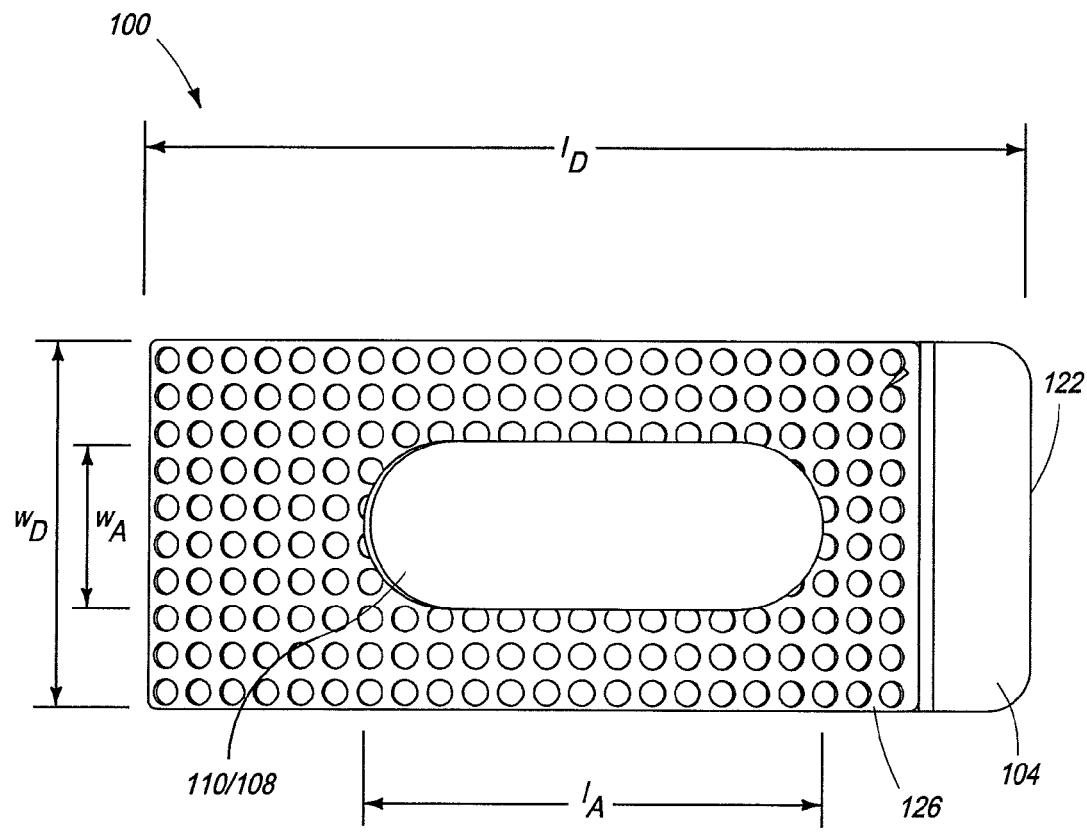
FIG. 4 is a top view of the interbody device of FIG. 1.
Figure 11:
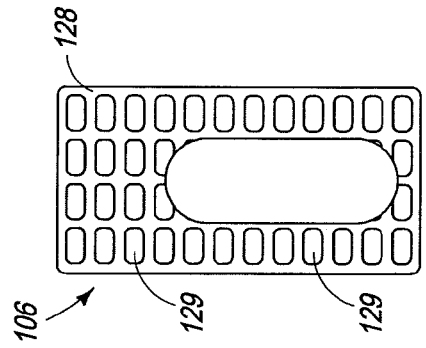
FIG. 11 is a top view of the inferior endplate of FIG. 9, showing a core interface side.
Figure 12:
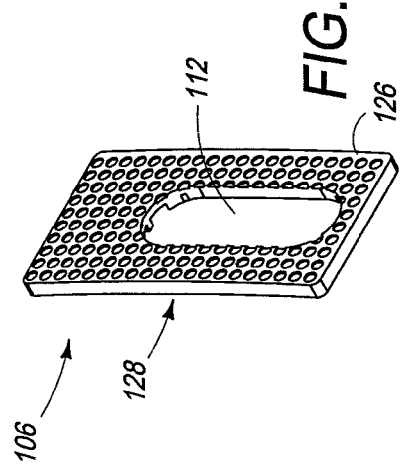
FIG. 12 is a perspective view of the inferior endplate of FIG. 9.
Figure 10:
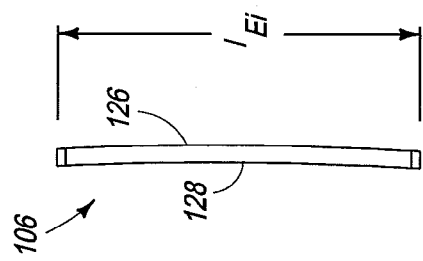
FIG. 10 is a side view of the inferior endplate of FIG. 9.
Figure 9:
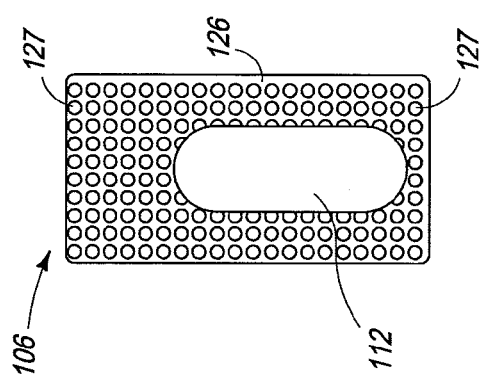
FIG. 9 is a bottom view of the inferior endplate of FIG. 1.

FIG. 4 is a simplified top view of device 100 showing bone interface side 126 of superior endplate 102, described further with respect to FIGS. 5-8. It will be appreciated, after reading the following description, that FIG. 4 may also represent a bone interface side of inferior endplate 106.

In an embodiment according to FIGS. 4-8, device 100 width ($w_D$) is about 11 mm. Aperture 110 of endplate 102 has an aperture length ($l_A$) of about 13-14 mm and an aperture width ($w_A$) of about 5-6 mm (FIG. 4). Endplate 102 has a superior endplate length ($l_{ES}$) of about 22-23 mm (FIG. 5). Bone interface side 126 of endplate 102 is for example HA-coated titanium, molybdenum or other biocompatible metal, which includes a plurality of holes or pores 127 into which bone may grow when device 100 is implanted. Bone interface side 126 is opposite a core interface side 128 (FIG. 6). Core interface side 128 faces core 104 and includes a plurality of holes or pores 129 for accepting material of core 104 to enhance adhesion to core 104. Pores 127 of bone interface side 126 are of optimal size for promoting bone in-growth. For example, pores 127 are about 600 microns in diameter. Pores 129 of core interface side 128 are larger than the pores 127 of bone interface side 126, to maximize bonding between core 104 and endplate 102. When injection molded between endplates 102 and 104, core 104 material penetrates core interface side 128 via the larger pores 129, to firmly bond endplate 102 with core 104. Pores 127 and 129 may be perforations or holes through sides 126 and 128, respectively, or pores 127 and 129 may be openings in a wire mesh forming sides 126 and 128. The terms pores, perforations and openings are used interchangeably, below.

Superior endplate 102 and inferior endplate 106 are curved or otherwise shaped for ease of insertion. However, endplates 102 and 106 may alternately be shaped to maximize contact between device 100 and adjacent bone (for example, endplate bone-interface sides 126 may be flattened to maximize surface area contact between endplates 102/106 and adjacent bone). As shown in FIGS. 1, 3, 8 and 12, endplates 102 and 106 are curved to mate with accepting vertebral surfaces at an implant site. The shape of device 100 therefore mimics an intervertebral space. Shape and size of device 100 and endplates 102/106 and/or core 104 may be altered to suit differently sized and shaped implant sites. Device 100 may be shaped to mimic a cavity created by a cutting tool used to prepare an implant site. For example, device 100 may be shaped to mimic a cavity reamed out by a ball mill to facilitate fusion at a hip, knee or shoulder joint.

FIGS. 9-12 show additional detail of inferior endplate 106, and are best viewed together with the following description. Like endplate 102, endplate 106 has a bone interface side 126 with pores 127 (that are for example about 600 microns) and a core interface side 128 with relatively larger pores 129 for accepting core 104 material. Bone interface side 126 may be hydroxyapatite-coated titanium, molybdenum or other biocompatible metal. Aperture 112 may be created by machining after molding, and is sized to permit access to vertically-oriented channel 108A of core 104, for example having dimensions similar to aperture 110 of superior endplate 102. Endplate 106 may be slightly shorter than endplate 102, having an inferior endplate length ($l_{EI}$) of about 21-22 mm. Endplates 102/106 are, for example, fabricated from a large sheet of bone interface side 126 material backed by core interface side 128 material that is cut into multiple endplates, which are then shaped as desired. For example, sheets of core interface side 126 material and bone interface side 128 material may be preliminarily bonded and cut into desired sizes for forming endplates 102/106. The cut sections may then be diffusion bonded to permanently join side 126 material with side 128 material at a molecular level, under heat and pressure. Endplates 102/106 may be curved or otherwise shaped as desired during or prior to diffusion bonding. As described below with respect to endplate assembly 200 (FIG. 19), a central barrier layer is inserted between side 126 material and side 128 material, to prevent core material that penetrates pores 129 of core interface side 128 from seeping into or clogging bone in-growth areas provided by pores 127 of side 126.

Figure 13:
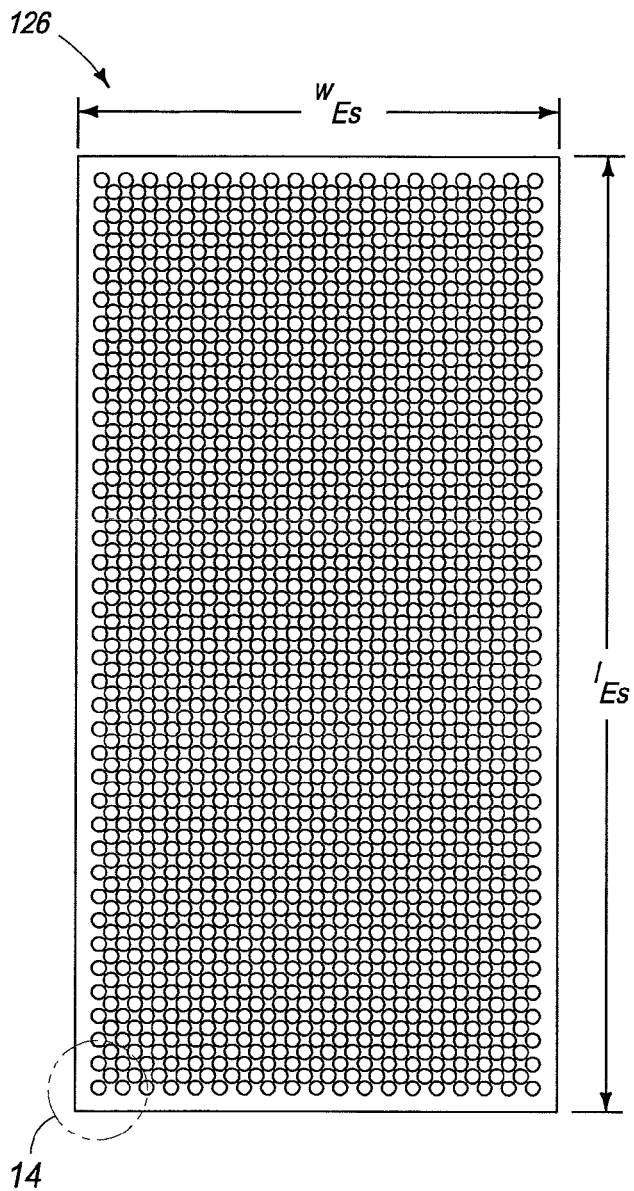
FIG. 13 is a schematic view of a bone interface layer of the superior or the inferior endplate of FIG. 1.
Figure 14:
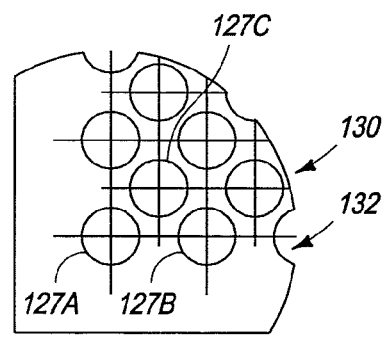
FIG. 14 is an enlarged view of an area of the bone interface layer of FIG. 13.

FIG. 13 is a top view of bone interface side 126 of endplate 102/106, and FIG. 14 shows additional detail of a section A of side 126. In one embodiment, bone interface side 126 is a thin sheet of titanium, and pores 127 are perforations through bone interface side 126. Perforations 127 have a diameter of about 0.30 mm and a center-to-center spacing of about 0.050 mm along a given row 130 or 132. For example, a distance from the center of perforation 127A to the center of perforation 127B in row 132 is about 0.30 mm. Perforations 127 of adjacent rows 130 and 132 are offset such that a center-to-center (diagonal) distance between perforation 127A in row 132 and perforation 127C in row 130 is about 0.030-0.045 mm. Perforations 127 may commence about 0.030-0.040 mm from edges of bone interface side 126.

As illustrated in FIGS. 15-18, in one embodiment, pores 129 of core interface side 128 are perforations through a thin sheet of titanium or other metal. Perforations 129 are optimized for accepting material of core 104 when core 104 is injection molded between core interface sides 128 of endplates 102/106. Perforations 129 are larger than pores 127, and may be elliptical to rectangular in shape. In one aspect, perforations 129 have a width ($w_P$) of about 0.050 mm and a length ($l_P$) of about 0.100 mm. Perforations 129 are for example spaced at about 0.050 mm from edges of side 128 and adjacent perforations are spaced about 0.010 mm apart.

Figure 15:
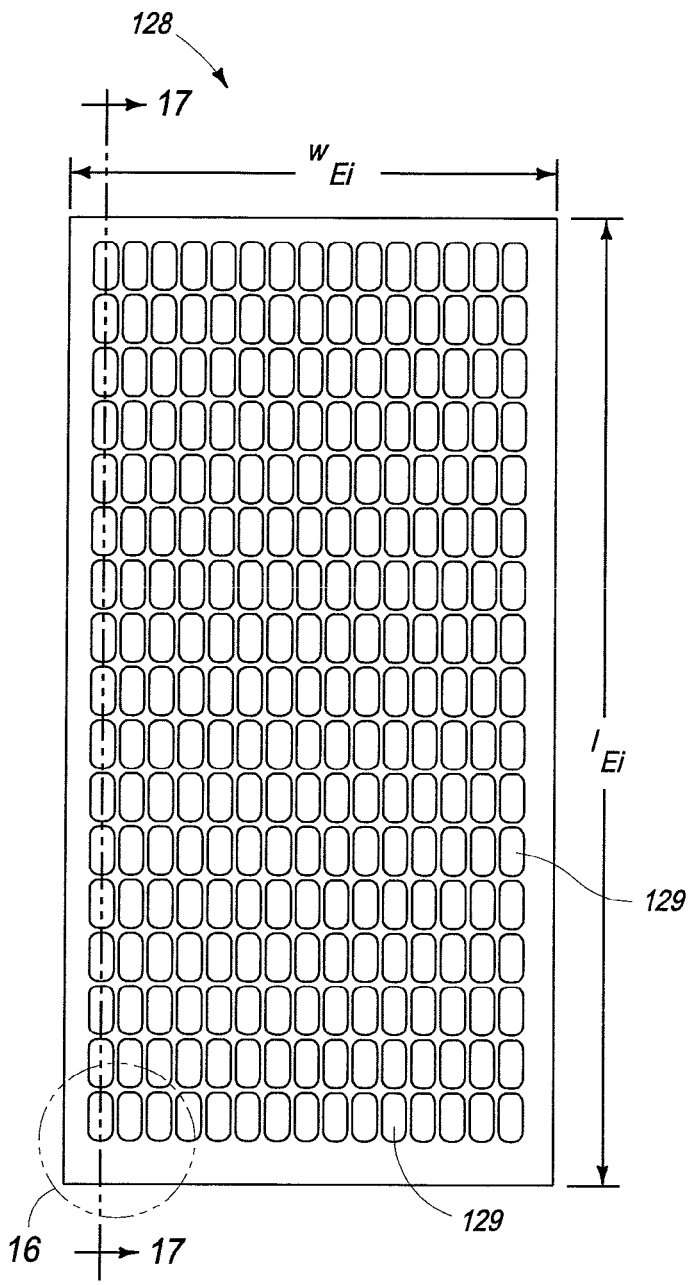
FIG. 15 is a schematic view of a core interface layer of the superior or the inferior endplate of FIG. 1.
Figure 16:
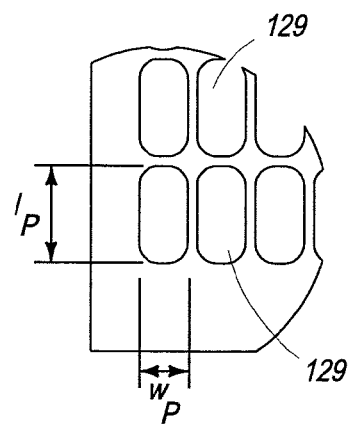
FIG. 16 is an enlarged view of a section of the core interface layer of FIG. 15.

FIG. 17 is a cross-sectional view of side 128, taken along line 17-17 of FIG. 15. FIG. 18 is an enlarged view of section B of FIG. 17, showing a side view of perforations 129.

Figure 19:
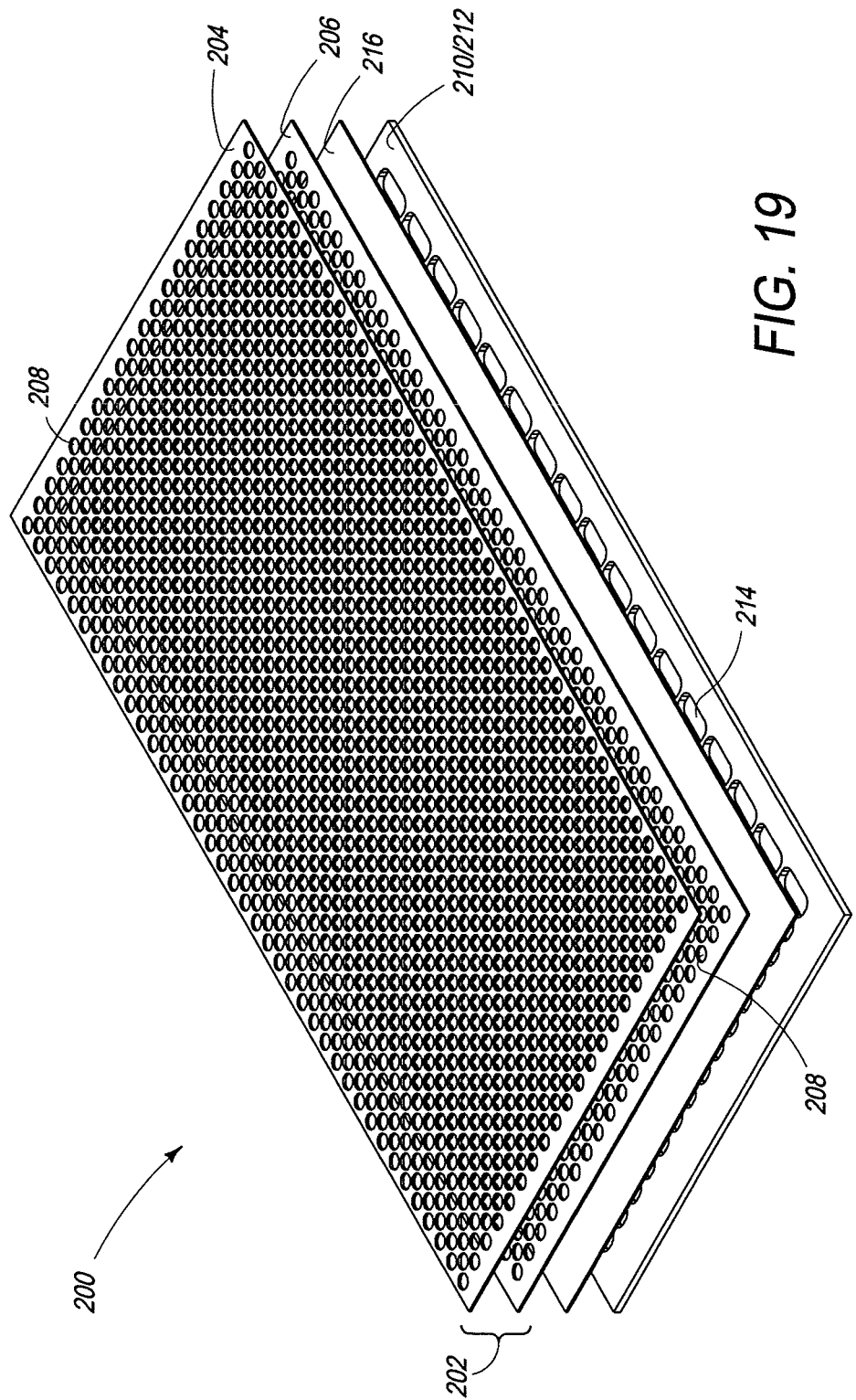
FIG. 19 is an exploded view showing layers forming an endplate of FIG. 1, according to an embodiment.
Figure 20:
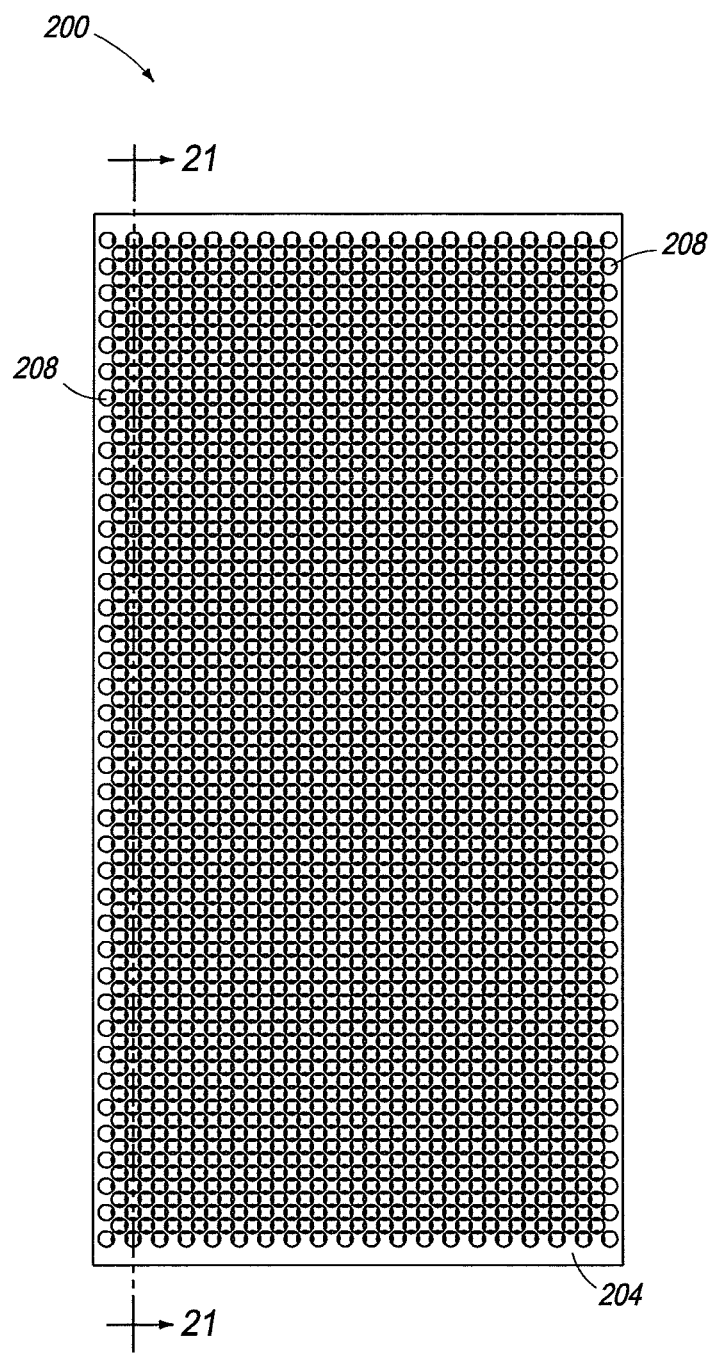
FIG. 20 is a top view of the endplate of FIG. 19, showing an outermost bone interface layer.
Figure 23:
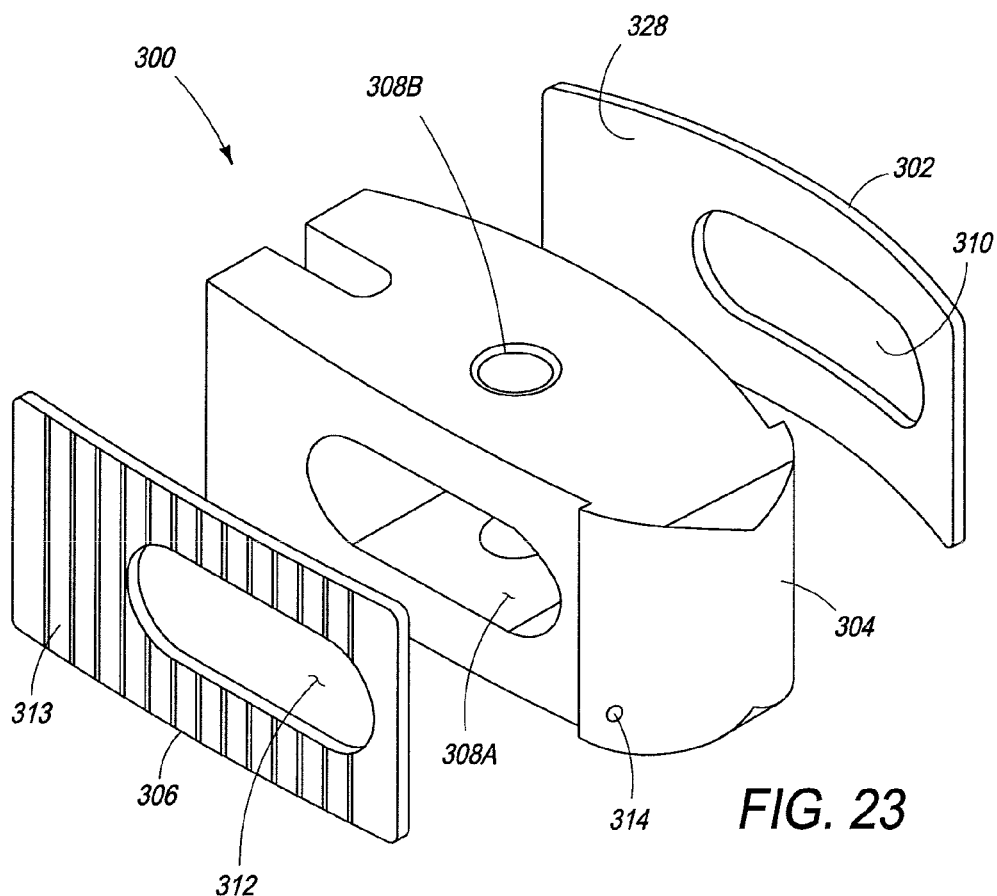
FIG. 23 is an exploded view of a composite interbody device having machine-featured superior and inferior endplates, in accordance with an embodiment.

FIG. 19 is an exploded view of an assembly 200 for forming endplate 102 and/or endplate 106 of interbody device 100, described above. FIG. 20 illustrates a bone interface side view of assembly 200. FIG. 21 is a cross-sectional illustration taken along line 21-21 of FIG. 20, and FIG. 22 is an enlarged view of a portion C of FIG. 21, showing additional detail of assembly 200 in cross-section. FIGS. 19-22 are best viewed together with the following description.

In an embodiment according to FIGS. 19-22, assembly 200 includes a bone interface side 202 including at least two bone interface layers 204 and 206. First and second bone interface layers 204 and 206 are shown in FIG. 19. Additional bone interface layers (e.g., for a total of four to five layers) may be added, to vary bone in-growth characteristics of side 202 and/or tensile strength or other characteristics of endplate 102 or 106 formed from assembly 200.

First and second layers 204 and 206 are for example coated with hydroxyapatite to encourage bone on-growth, and are formed of titanium wire mesh of an optimal size for bone in-growth (e.g., the mesh provides pores 208 of about 600 microns diameter). The wire of the mesh is for example 0.5 mm titanium wire, and provides relatively low porosity and relatively high flow restriction as compared with a core interface side 210. Pores 208 may alternately take on a square, rectangular or other shape having minor dimensions of about 600 microns (e.g., the width of a rectangular pore) and major dimensions of no more than approximately three times the minor dimensions (e.g., the rectangular pore is no longer than about 1800 microns).

Core interface side 210 lies opposite bone interface side 202 and includes at least one core interface sheet 212 of titanium or other biocompatible metal. Sheet 212 includes perforations or pores 214 that are larger than pores 208 of side 202, to maximize bonding between an endplate formed with assembly 200 and an interbody core such as core 104, or another interbody device, such as an artificial disc.

Core interface sheet 212 may be a mesh formed with larger-gauge wire than the mesh of layers 204 and 206, or with a looser-weave mesh to provide relatively larger pores, higher porosity and lower flow restriction than side 202. Higher porosity and lower flow restriction enhance flow of material from an interbody core/device (i.e., core 104 material) into pores 214 of side 210, to encourage bonding between an endplate (i.e., endplate 102/106) formed with assembly 200 and the core/device. It will be appreciated that although a single sheet 212 makes up core interface side 210 in FIG. 19, side 210 may include multiple sheets 212 of larger-gauge titanium wire mesh.

Alternately, side 210 includes one or more perforated or micro-etched core interface sheets 212 with pores sized to encourage bonding between an endplate (e.g., endplate 10/106) formed with assembly 200 and an interbody core/device. A central plate or layer 216 between side 202 (layers 204 and 206) and side 210 (sheet 212) prevents material from the interbody core/device (e.g., PEEK of core 104) from over-extruding into endplate 102/106. Central layer 216 for example prevents PEEK or other core 104 material from flowing all the way through endplate 102/106, blocking the plastic from flowing into bone interface layers 204 and 206 and thus maintaining the bony in-growth spaces provided by pores 208.

Assembly 200 is diffusion bonded, by placing layers 204, 206, 212 and 216 into a die and applying heat and pressure to create an artificial porous matrix. Diffusion bonding at an atomic level facilitates combination of surfaces that touch one another, and results in near 100% bonding. Diffusion bonding may occur prior to forming endplates 102/106 from assembly 200. For example, assembly 200 may be formed as a 50 mm by 25 mm by 0.75 mm composite sheet (or an alternately sized composite sheet), and endplates 102/106 may be cut from assembly 200 after diffusion bonding. Alternately, endplates 102/106 are cut from assembly 200 (which may be preliminarily bonded) or assembly 200 is sized to the requirements of endplates 102/106, prior to diffusion bonding. Since diffusion bonding does not require flat sheets, unique curvatures of either or both endplates 102/106 are accommodated. Curvature may be integrated into dies for diffusion bonding to allow customization of endplates 102/106 for any interbody device/core (such as core 104) and/or any accepting bony surface. For example, endplates 202 and 206 may be diffusion bonded in a press to produce a desired endplate shape or contour. During manufacture, endplates 102/106 may also be mirrored or trimmed to suite multiple sizing requirements.

In one embodiment, dual assemblies 200 are sized according to sizing requirements for endplates 102 and 106. Assemblies 200 are positioned into a mold with core interface sides 210 facing a cavity for core material (e.g., core 104 material or material for forming an artificial disc or another interbody device configured for bonding with endplates 102/106). Core material (e.g., PEEK) is injection molded between assemblies 200 and penetrates pores 214 of core interface side 210, to firmly bond with assembly 200 (endplates 102/104). Central layer 216 prevents core material from over-extruding into pores 208 of layers 204 and 206, thus preserving bone in-growth spaces of bone interface side 202. As shown in FIG. 22, pores 208 of layers 204 and 206 may be selectively offset to optimize side 202 for bone in-growth.

Once set, the shape and geometry of the interbody core/device (e.g., core 104) may be refined by machining out of composite blanks. For example, features 108 are machined into core 104 after molding (see FIG. 1). Hydroxyapatite is surface treated onto bone interface side 202 of endplates 102/106, before or after core 104 is injection molded therebetween, to promote bone on-growth and in-growth onto and into bone interface side 202. Hydroxyapatite may be spray-coated, painted or otherwise applied to bone interface sides 202. Depth of the hydroxyapatite coating may be varied to achieve optimal on-growth/in-growth efficiency, or according to an intended implant location. The metal-PEEK-metal (e.g., titanium-PEEK-titanium) combination of device 200 is less stiff than a primarily titanium implant and thus reduces stress shielding.

In one embodiment, titanium sheets formed with perforations and/or texture replace the mesh forming one or both of layers 204 and 206. Layers 204 and 206 may be selectively micro-perforated or photo etched to provide pores 208 and/or other texturizing features. For example, layers 202 and 204 are etched with 500 micron (40-mil) perforations/pores 208 using a photo etching process capable of a resolution of 5 mil (0.125 mm). Side 202 may thus be formed as a matrix of sequentially stacked titanium perforations/pores 208. Selective placement of titanium perforations/pores 208 on side 202 and larger pores 214 on side 210 allows porosity control for regulating/encouraging both bone in-growth and PEEK bonding. For example, porosity may be controlled to produce pores 208 of approximately 500-600 microns, for ideal bone in-growth.

FIGS. 23-26 show an interbody device 300 having machine-featured superior and inferior endplates 302 and 306, flanking a core 304. Core 304 may be similar to core 104 of FIG. 1. Core 304 includes multiple features 308, such as vertically-oriented channel 308A running top-to-bottom through core 104, and a horizontally-oriented channel 308B running side-to-side through core 104. Features 308A and 308B facilitate bone growth through core 304/device 300, and may be packed with bone and/or other materials to enhance fusion (e.g., proteins or other materials to enhance bone growth, or fusion enhancing glues). A slot 308C in a back side (distal to the spinal cord when inserted between vertebrae) of core 304 is sized to fit an insertion tool, to facilitate insertion of device 300 between adjacent vertebrae. Features 308A-C may be machined after core 304 is molded (e.g., after injection-molding core 104 between endplates 302 and 306) or features 308A-308C may be extruded or otherwise formed.

Figure 24:
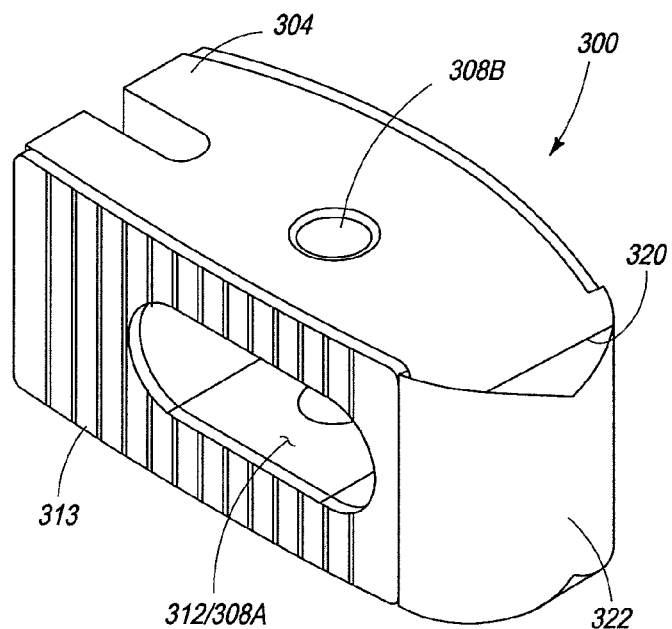
FIG. 24 is a perspective view of the composite interbody device of FIG. 23, as assembled.
Figure 25:
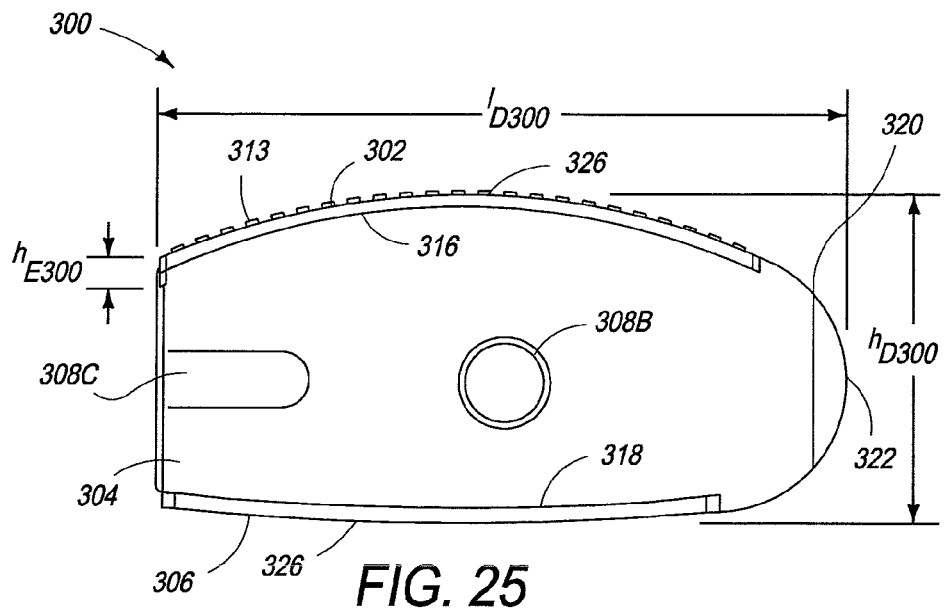
FIG. 25 is a side view of the assembled interbody device of FIG. 24.
Figure 26:
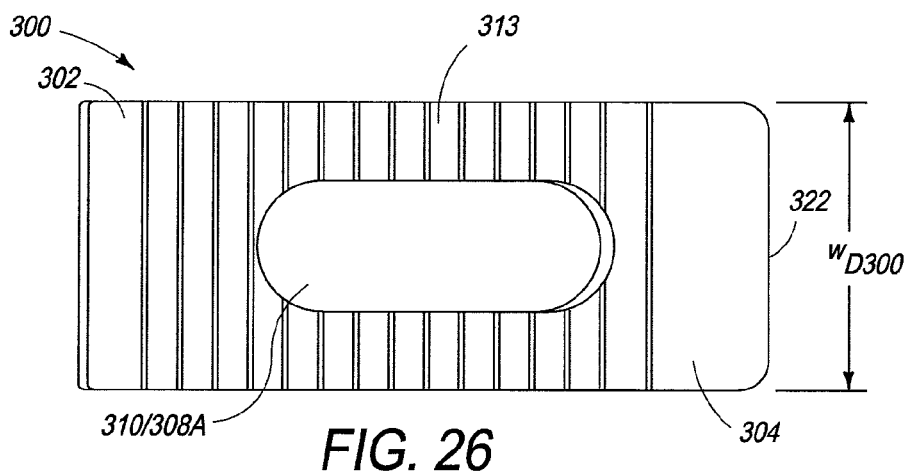
FIG. 26 is a bone-side view of the superior or inferior endplate of FIGS. 23 and 24.
Figure 27:
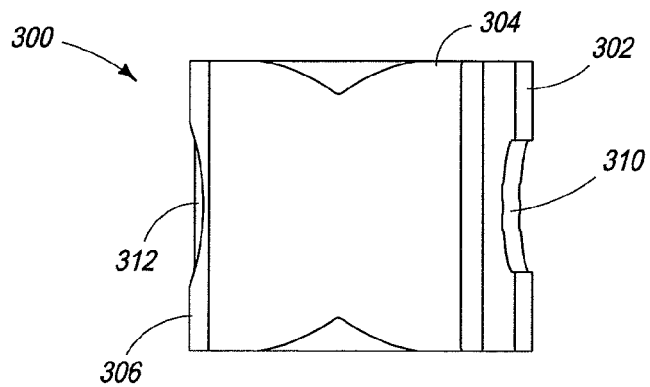
FIG. 27 is an insertion end view of the device of FIG. 24.

Channel 308A aligns with an aperture 310 in superior endplate 302 and with an aperture 312 in inferior endplate 306 when device 300 is assembled as shown in FIG. 24. It will be appreciated that any fusion aids for insertion into device 300 may be loaded via aperture 310 or aperture 312. Where core 304 is formed of radiolucent material, such as PEEK plastic, one or more radio markers 314 may be incorporated to facilitate visualization of core 304 on x-ray, for example once device 300 is implanted. Endplate 302 bonds with a superior endplate contact surface 316 of core 304, and endplate 306 bonds with an inferior endplate contact surface 318, as shown in FIG. 25. Core 304 may taper from a bevel line 320 to a nose 322, to facilitate insertion of device 300 into an intervertebral space or other implant site.

Endplates 302 and 306 are curved as a result of forming and diffusion bonding in a press to conform to a desired shape of core 304 and/or an accepting bony surface. In one aspect, endplates 302 and 306 are multi-surface machined yielded titanium plates with geometric features protruding therefrom, to increase relative endplate surface area for bone on-growth on bone interface sides 326 (see FIG. 25). Ridges 313 are shown in FIGS. 23-27 for ease of illustration; however, it will be appreciated that ridges 313 are representative only and may be replaced or supplemented by thin webs or other geometries. For example, endplates 302 and 306 may bear geometric features resulting from fracturing (i.e., pulling apart) a titanium plate. Such endplates may advantageously be formed in a one-step manufacturing process, thereby reducing overall cost of the interbody device.

Alternately, although not shown, core interface sides 328 of endplates 302 and 306 may also bear geometric features for increasing surface area of core interface sides 328 to enhance bonding with core 304 material. Alternately, a porous titanium layer, such as sheet 212 (see FIG. 19) may be diffusion bonded with a back (un-featured) surface of a single titanium sheet having ridges 313 or other features on its opposite side. For example, core interface side 328 may include a sheet of titanium wire mesh or perforated titanium that is diffusion bonded with a back surface of bone interface side 326. In such configuration, no central barrier layer is required.

Device 300 length ($l_{D300}$) and height ($h_{D300}$), shown in FIG. 25, are for example similar to length ($l_D$) and height ($h_D$) of device 100 (see FIGS. 2-3). Device 300 width ($w_{D300}$), shown in FIG. 26, may also be similar to width ($w_D$) of device 100.

Figure 28:
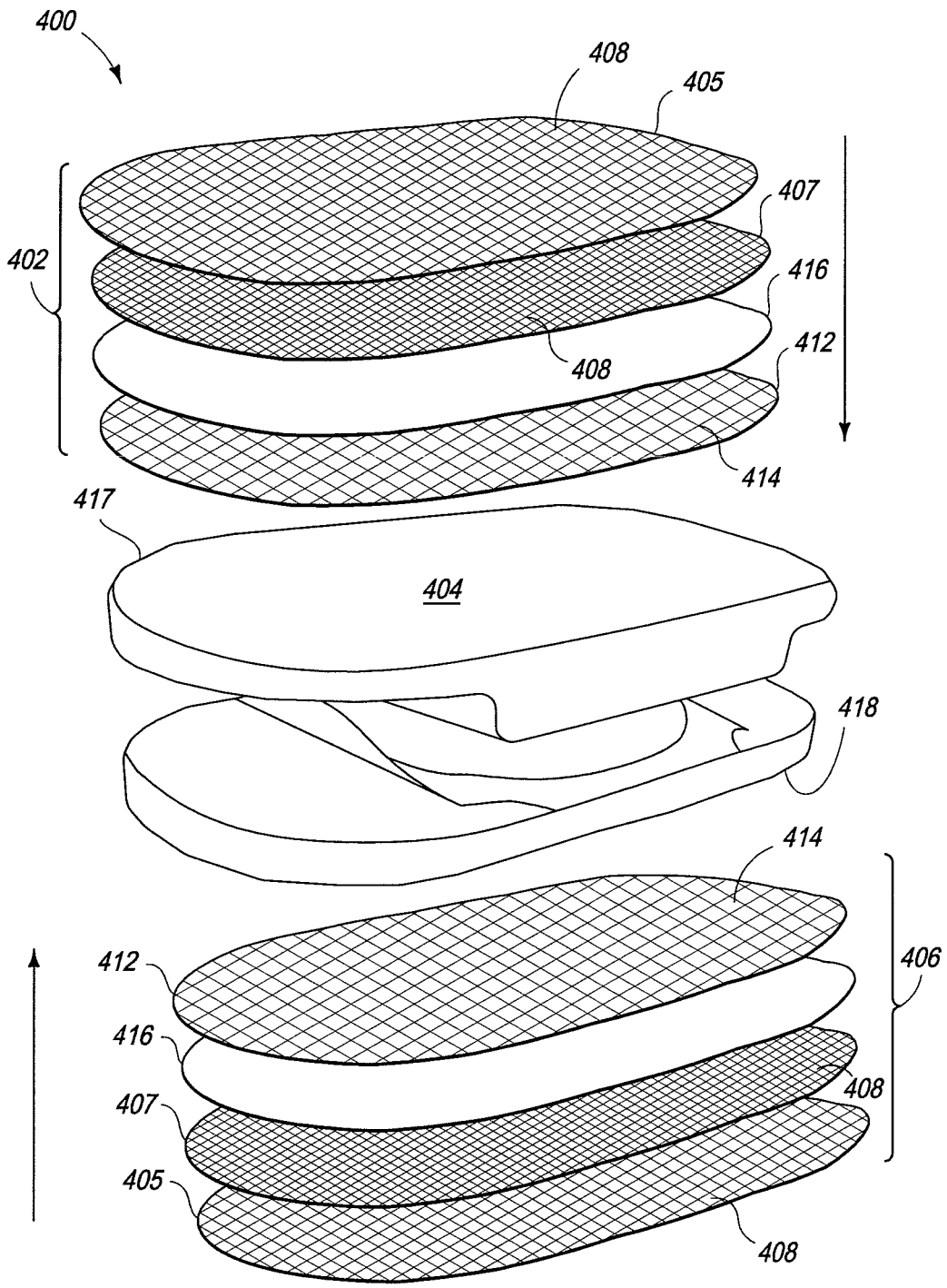
FIG. 28 is an exploded perspective view showing composite layers forming the endplates of FIG. 1 as applied to an artificial disc, according to an embodiment.

FIG. 28 is an exploded perspective view of an interbody device 400, showing composite layers forming superior and inferior endplates 402 and 406, as applied to an artificial disc 404. In one embodiment, endplates 402 and 406 each include bone interface layers 405 and 407 selectively placed, one layer relative to the other, to optimize bone in-growth spaces provided by pores or perforations 408 of layers 405 and 407. A disc interface layer 412, having relatively larger pores 414 (as compared with pores 408), is separated from layers 405 and 407 by a central barrier layer 416 that is for example a thin sheet of solid metal. Larger pores 416 admit flow of artificial disc 404 material therein. For example, molten or softened plastic forming disc 404 may extrude into pores 414 to maximize contact and bonding between disc 404 and layer 412, and thus between disc 404 and endplates 402 and 406. Central barrier layer 416 prevents material of disc 404 from flowing into pores 408, thus reserving pores 408 for bone in-growth.

Bone interface layers 405 and 407, disc interface layer 412 and central barrier layer 416 are made of a biocompatible metal such as titanium. In one embodiment, bone interface layers 405 and 407 are HA-coated titanium wire mesh having pores 408 formed by spaces between small gauge (e.g., 0.5 mm) titanium wire. However, a perforated, HA-coated titanium sheet may replace one or both of bone interface layers 405 and 407. Central barrier layer 416 is a solid sheet of titanium, and core interface layer 414 is a sheet of titanium mesh having larger pores than bone interface layers 405 and 407, to enhance bonding with artificial disc 404.

Endplates 402 and 406 may be applied layer-by-layer to superior and inferior endplate contact surfaces 417 and 418 of core 404. For example, disc interface layer 412 is first applied to superior endplate contact surface 417. Central barrier layer 416 is applied to layer 412, and titanium/HA bone interface layers 407 and 405 are applied to central barrier layer 416. Layers 405 and 407 may be selectively placed to optimize interface between sheets, and to optimize porosity (i.e., alignment of pores 408 of each layer 405, 407) for bone in-growth. Although not shown, layers 405 and 407 may themselves each include multiple sublayers (e.g., 4-5 sublayers) of titanium wire mesh to provide further lower porosity and raise flow restriction. Contact surfaces 417 and 418 may be PEEK plastic, titanium, cobalt chrome or alloy surfaces of artificial disc 404, the remainder of which may be configured of the same material or an alternate material as contact surfaces 417 and 418. Any of bone interface layers 405, 407 and central barrier layer 416 may be diffusion bonded to one another or to disc interface layer 412. Where artificial disc 404 includes metallic contact surfaces 417 and 418, all layers of endplates 402 and 406 may be diffusion bonded directly to the metallic contact surfaces.

Artificial disc 404 may also be molded between pre-assembled endplates 402, 406, as described above with respect to core 104 of interbody device 100.

Layers 405, 407, 416 and 412 may optionally be pre-formed into single composite endplates 402/406 that are shaped (i.e., via simultaneous forming and diffusion bonding in a press) to complement respective contact surfaces 417 and 418, and that are applied in single operations to superior endplate contact surface 417 and to inferior endplate contact surface 418. One exemplary disc suitable for application of layers 405, 407, 416 and 412 (or endplates 402/406 formed therefrom) is a Pioneer NuBak PEEK on PEEK disc. Endplates 402 and 406 may be shaped to compliment a shape of disc surfaces 417 and 418, or disc 404 may be injection molded between the endplates, with disc 404 conforming to the shape of the endplates.

Figure 29:
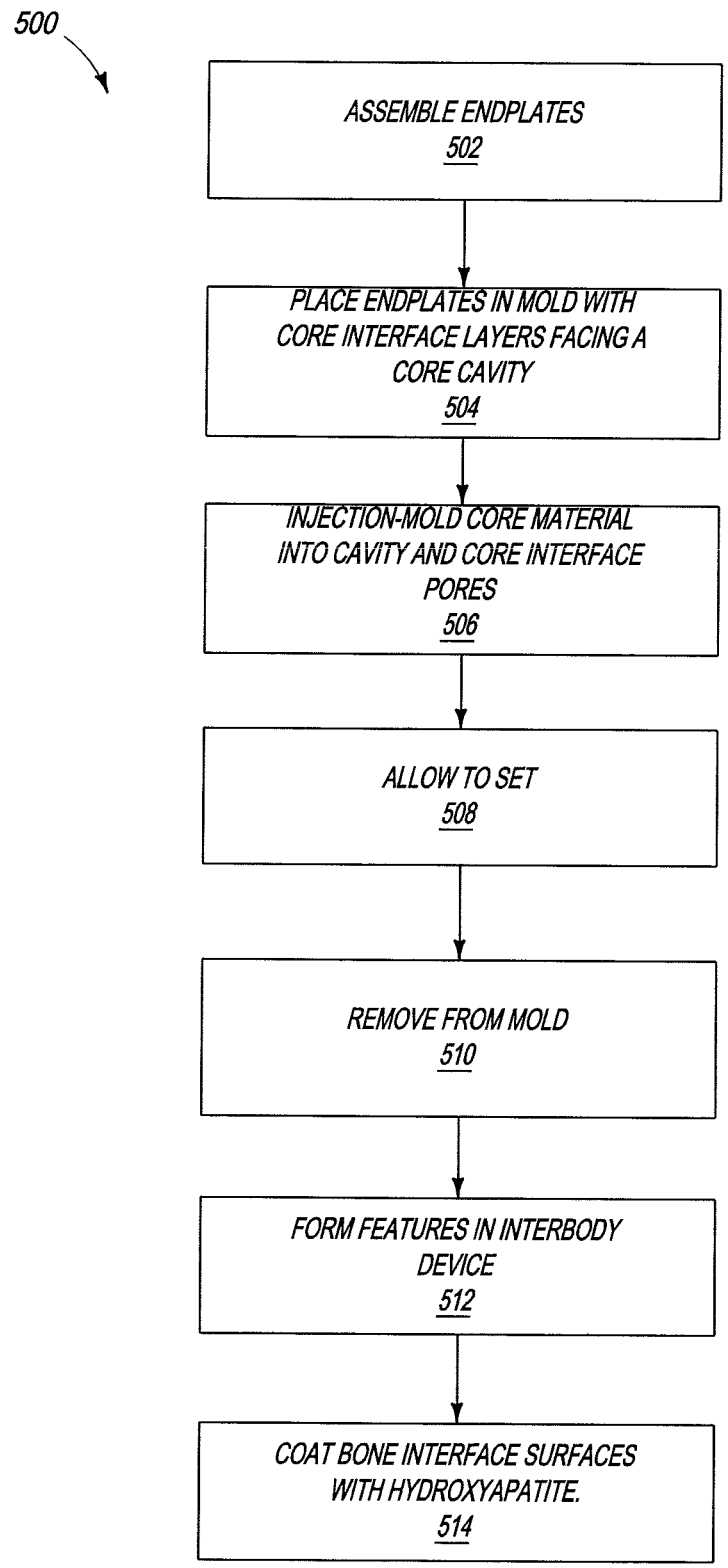
FIG. 29 is a flowchart showing a method of forming an interbody device, according to an embodiment.

FIG. 29 illustrates one method 500 for forming an interbody device, such as device 100. Inferior and superior endplates are assembled, in step 502, and placed in a mold with core interface layers facing a core cavity, in step 504. Core material is injection molded into the cavity and, through the cavity, into pores of the core interface side, in step 506. In one example of steps 502-506, endplates 102 and 106 are assembled as described with respect to FIG. 19 (assembly 200). The endplate-core-endplate assembly is allowed to set (for example, the assembly may be cooled until the core fully hardens), in step 508, and removed from the mold, in step 510. Features are formed in the interbody device, in step 512. In one example of step 512, features 108A-108C and apertures 110 and 112 are formed in device 100. For example, one channel may be drilled through device 100 to form aperture 110, channel 108A and aperture 112. Bone interface surfaces of the device (i.e., bone interface surfaces 126, see FIG. 3) are coated with hydroxyapatite, in step 514. It will be appreciated that although shown as a final step in FIG. 29, hydroxyapatite may alternately or additionally be coated onto bone interface surfaces prior to their incorporation into endplates 102 and 106, or after formation of the endplates and prior to placement in the mold.

Figure 30:
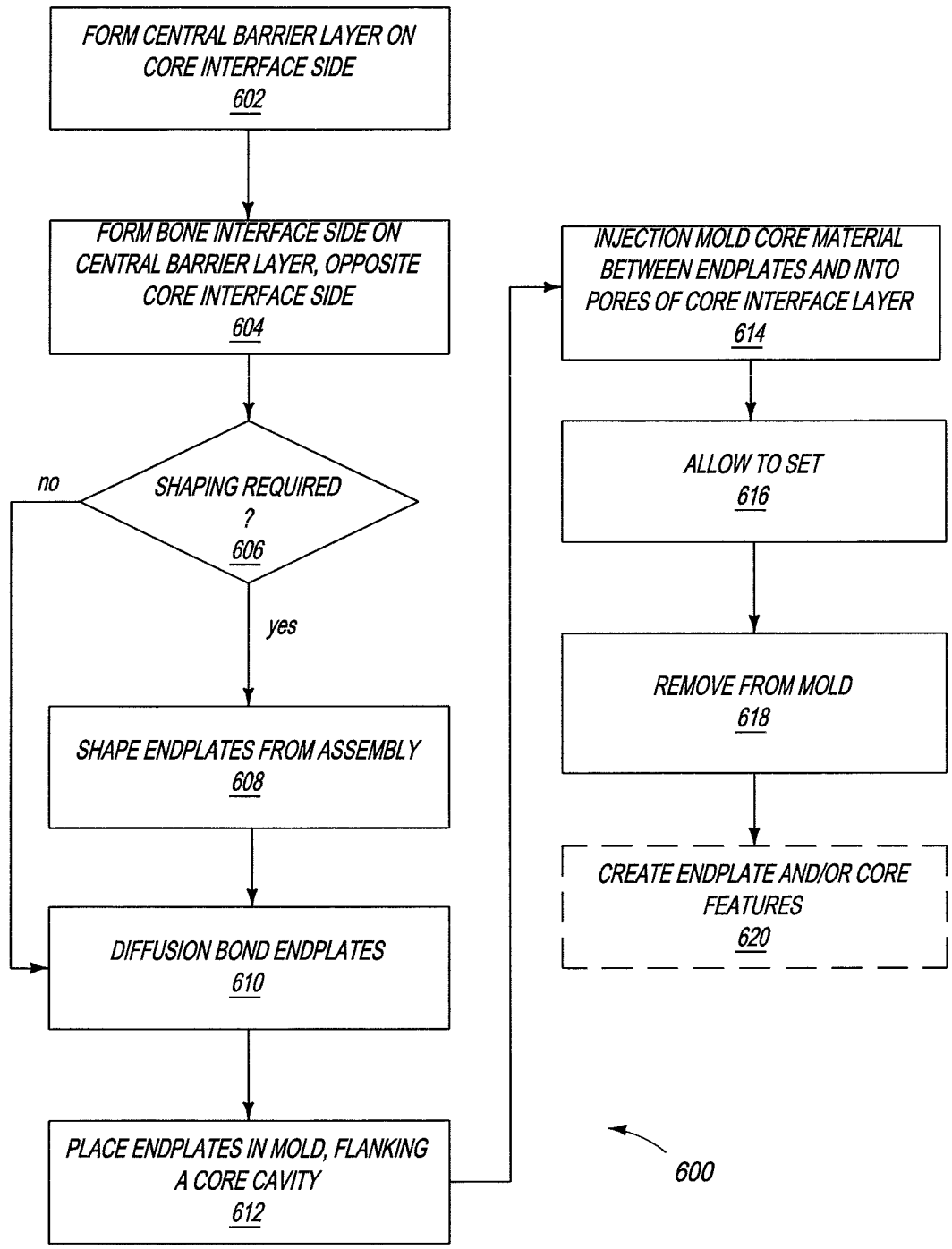
FIG. 30 is a flowchart illustrating another method of forming an interbody device, according to an embodiment.

FIG. 30 shows a method 600 for forming an interbody device. Method 600 is for example used to form device 100, with an assembly such as assembly 200 used to form endplates 102 and 106. A central barrier layer is formed on a core interface side, in step 602, and a bone interface side formed on the central barrier layer, opposite (e.g., on an opposite side from) the core interface side, in step 604. In one example of steps 602-604, central layer 216 is placed on core interface side 210, and bone interface side 202 is placed on central layer 216 (FIG. 19). If shaping is required (decision 606), for example if endplates such as endplates 102 and 106 are to be cut from a larger assembly of sides 202 and 210 and central layer 216, then endplates are shaped from the assembly, in step 608. The endplates are diffusion bonded, in step 610, and placed into a mold with core interface sides facing a cavity, in step 612. In one example of steps 606-612, endplates 102 and 106 are cut from a larger master sheet of preliminarily bonded side 202, central layer 216 and core side 210, and diffusion bonded under heat and pressure, prior to placement in a mold having a cavity sized and shaped for forming core 104. In another example, a master sheet of side 202, central layer 216 and core side 210 is diffusion bonded prior to cutting or otherwise shaping endplates 102 and 106 from the master sheet. The endplates are then placed into a mold as described.

In step 614, core material is injection-molded into the core cavity, and allowed to extrude into pores of the core interface side. The molded assembly is allowed to set until hardened, in step 616, and removed from the mold, in step 618. Endplate and/or core features may be created in the hardened interbody device, in step 620. In one example of steps 614-620, material of core 104, such as molten PEEK plastic, is injection molded into the core cavity and allowed to extrude into perforations or pores 214. Central barrier layer 216 prevents the core 104 material from extruding into pores 208 of side 202, thus reserving pores 208 as bone in-growth spaces. Once hardened, apertures 110 and 112 may be formed in superior and inferior endplates 102 and 106 (respectively), and channel 108A, channel 108B and aperture 108C may be formed in core 104. For example, apertures 110 and 112 and channel 108A may be formed in a single drilling or other machining operation through interbody device 100. Optionally, certain features of core 104 may be produced via a specially shaped mold having one or more mandrels for producing passages in the molten PEEK plastic.

Figure 31:
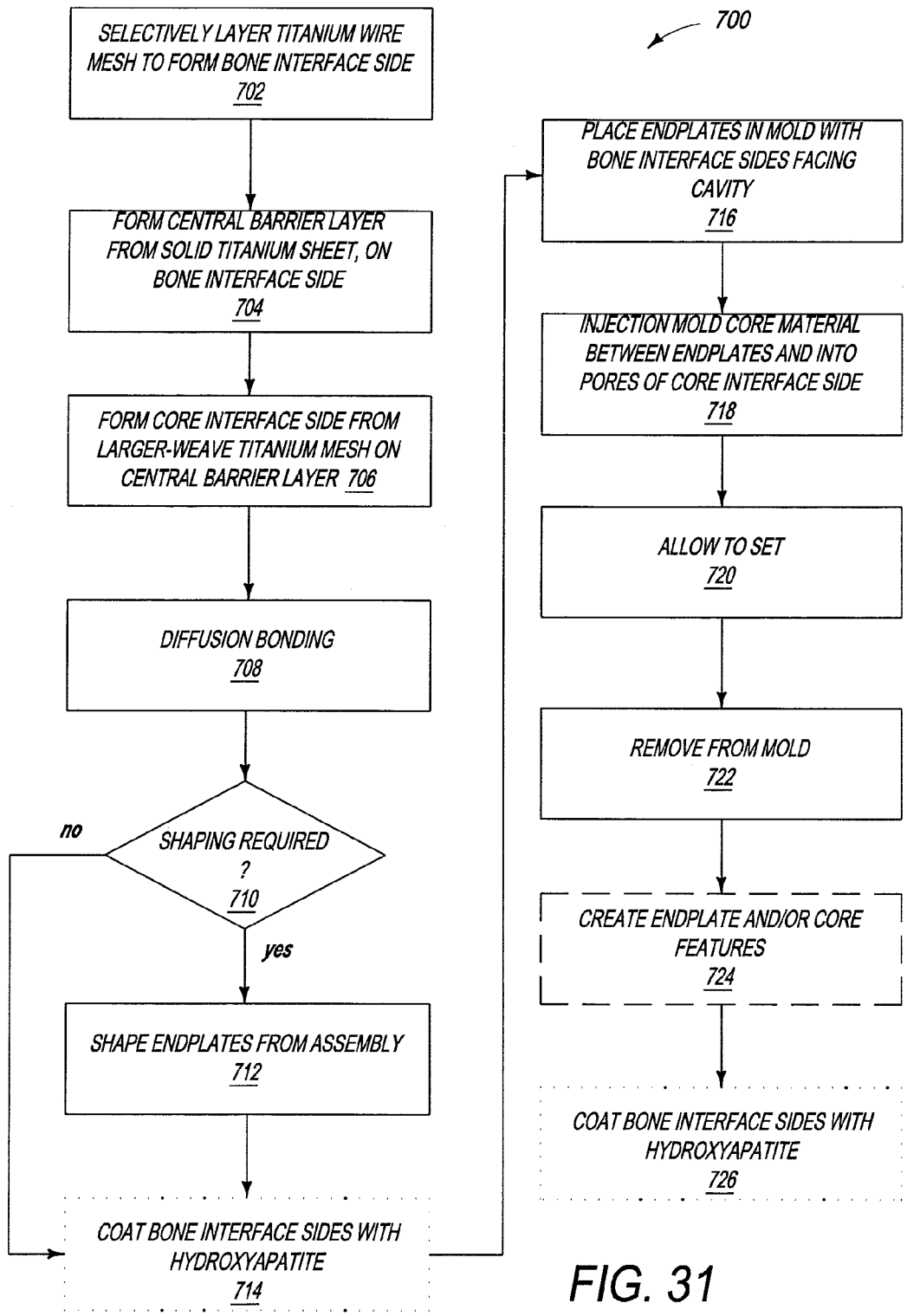
FIG. 31 is a flowchart showing a method of forming an interbody device, according to an embodiment.

FIG. 31 illustrates a method 700 of forming an interbody device, such as device 100, the endplates of which may be formed from assembly 200. In step 702, titanium wire mesh is selectively layered to form a bone interface side. A central barrier layer is formed from a solid titanium sheet, on the bone interface side, and a core interface layer is formed from larger-weave titanium mesh, on the central barrier layer, in steps 704 and 706. In one example of steps 704-706, bone interface side 202 is formed by selectively placing together titanium wire mesh layers 204 and 206, such that the pores 208 formed by openings in the mesh are at a desired orientation, one layer relative to the other. Central layer 216, which is for example a solid titanium sheet, is placed with side 202, and at least one core interface sheet 212 is placed with the opposite side of central layer 216, to form bone interface side 210. As noted above, pores 214 of sheet 214 are larger than pores 208, to reduce flow restriction on the core interface side.

The bone interface side, barrier layer and core interface side (e.g., side 202, central layer 216 and side 210) are diffusion bonded together, in step 708. If shaping is required (decision 710), endplates (e.g., endplates 102 and 106) are shaped from the bone interface side/barrier layer/core interface side assembly, in step 712, and optionally coated with hydroxyapatite on their bone interface sides, in step 714. Step 714 is illustrated as a dotted box to indicate that hydroxyapatite coating may take place at other points in method 700, for example at position 726 or elsewhere.

The endplates are placed in a mold with their bone interface sides facing a core cavity, in step 716, and core material is injection molded between the endplates, and allowed to extrude into the pores (e.g., mesh openings) in the core interface side, in step 718. After setting (Step 720), the interbody device is removed from the mold, in step 722, and endplate and/or core features are created, in optional step 724. In one example of steps 716-724, endplates 102 and 106 are placed into a mold with sides 210 facing an adjacent cavity. Molten material of core 104 (e.g., PEEK plastic) is injected into the mold and allowed to penetrate pores 214. After the PEEK is allowed to set, the rough interbody device is removed from the mold, and apertures 110 and 112 are formed in endplates 102 and 106, and any of features 108A-108C that were not formed in molding 104 are machined into core 104. For example, apertures 110, 112 and channel 108A are drilled through device 100.

Bone interface sides (e.g., sides 202) are coated with hydroxyapatite after the interbody device is machined with its desired features, after the endplates are shaped from the bone interface side/barrier layer/core interface side assembly, or both. Alternately, mesh layers forming the bone interface side may be coated with hydroxyapatite prior to placing the layers together to form the bone interface side, or the bone interface side may be coated with hydroxyapatite prior to its placement with the central barrier layer. The depth and placement of hydroxyapatite coating may vary as a function of an intended implant site.

Figure 32:
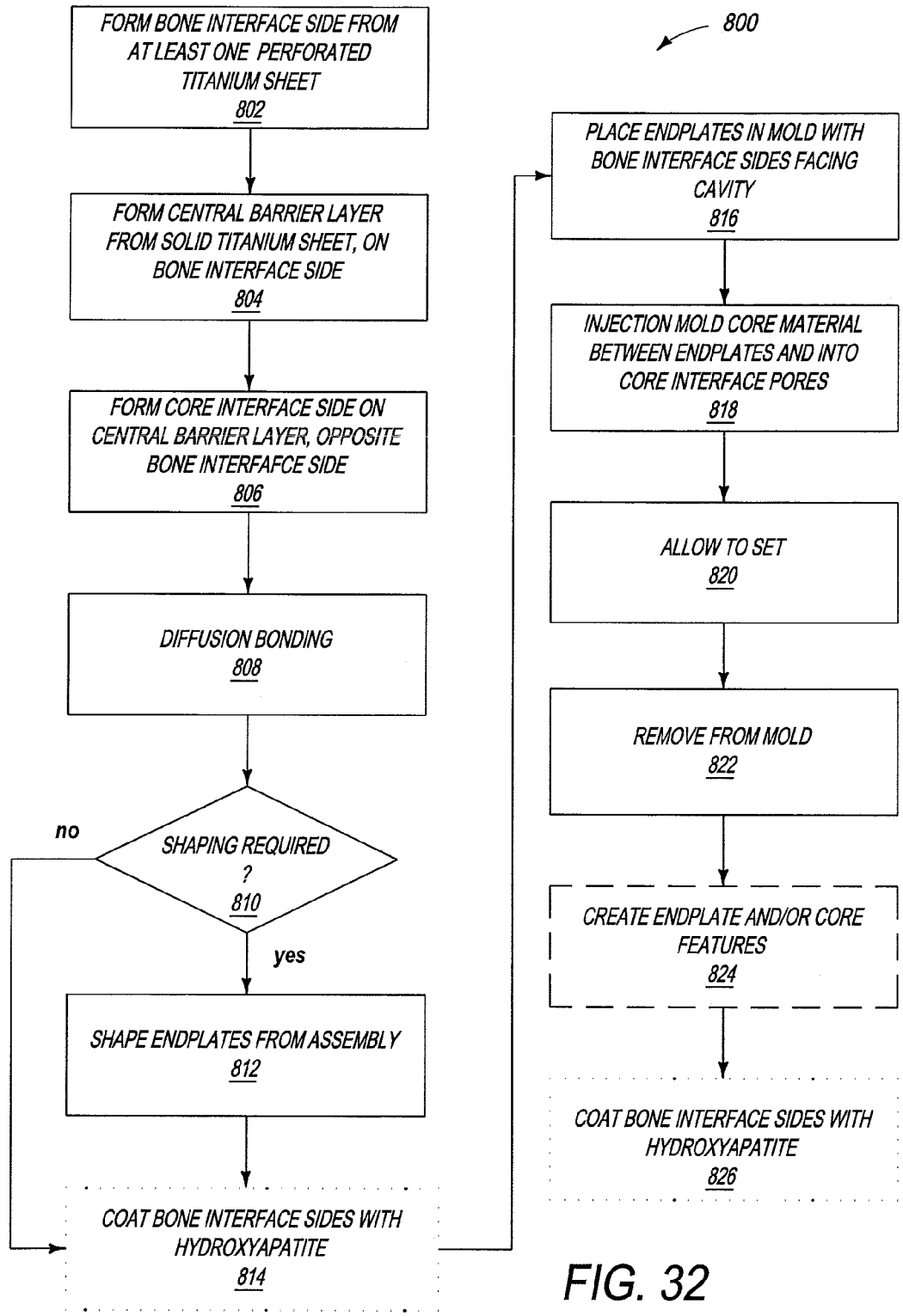
FIG. 32 is a flowchart showing a method of forming an interbody device, according to an embodiment.

FIG. 32 illustrates a method 800 of forming an interbody device. Method 800 may be used to form device 100 using assembly 200 to make endplates 102 and 106. A bone interface side is formed from at least one sheet of perforated titanium, in step 802, and a central barrier layer formed from a solid sheet of titanium is placed on the bone interface side, in step 804. A core interface side is formed on the central barrier layer, opposite the bone interface layer, in step 806. In one example of steps 802-806, bone interface side 202 is formed by selectively placing a plurality of perforated titanium sheets together such that the perforations are at a desired orientation, one layer relative to the other. See also FIGS. 5-8, showing perforated bone interface side 126 with perforations 127.

Central layer 216, which is for example a solid titanium sheet, is placed with side 202, and at least perforated titanium sheet 212 is placed with the opposite side of central layer 216, to form bone interface side 210. Perforations 214 of sheet 212 are larger than perforations 208, to reduce flow restriction on the core interface side.

The bone interface side, barrier layer and core interface side (e.g., side 202, central layer 216 and side 210) are diffusion bonded together, in step 808. If shaping is required (decision 810), endplates (e.g., endplates 102 and 106) are shaped from the bone interface side/barrier layer/core interface side assembly, in step 812, and optionally coated with hydroxyapatite on their bone interface sides, in step 814. Step 814 is illustrated as a dotted box to indicate that hydroxyapatite coating may take place at other points in method 700, for example at position 826 or elsewhere.

The endplates are placed in a mold with their bone interface sides facing a core cavity, in step 816, and core material is injection molded between the endplates, and allowed to extrude into the pores (e.g., mesh openings) in the core interface side, in step 818. After setting (Step 820), the interbody device is removed from the mold, in step 822, and endplate and/or core features are created, in optional step 824. Bone interface sides are coated with hydroxyapatite in step 826, if not already coated, or if additional coating is desired. Steps 816-826 are similar to steps 716-726, described in greater detail above.

Figure 33:
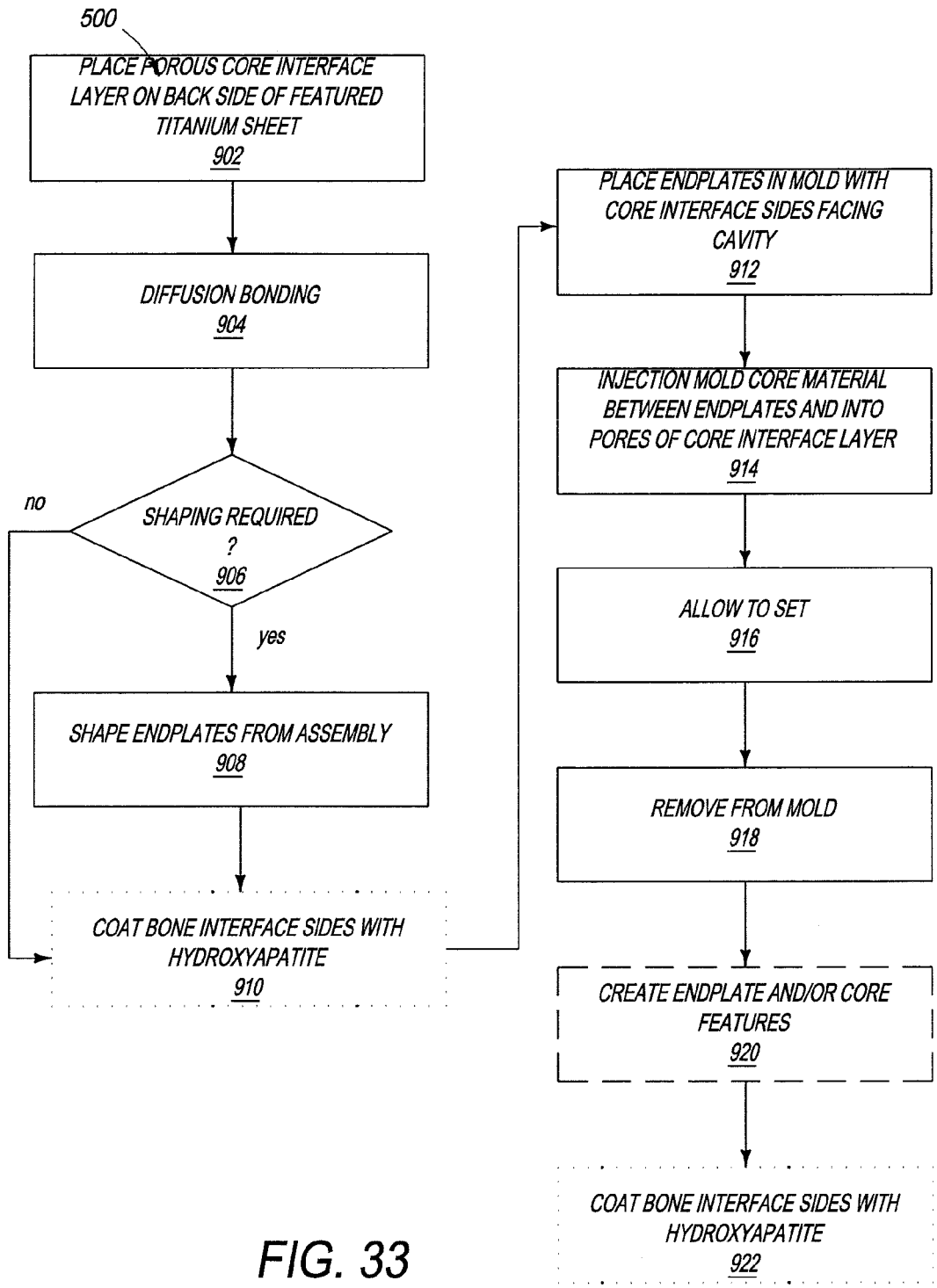
FIG. 33 is a flowchart illustrating a further method of forming an interbody device, according to an embodiment.

FIG. 33 shows a further method for forming an interbody device, such as device 300. A porous core interface layer is placed on the back side of a featured titanium sheet, in step 902, and the two are diffusion bonded together, in step 904. In one example of steps 902-904, porous sheet 212 is placed on core interface side 328 of material forming endplate 302 or 306 (FIG. 24), and the porous sheet is diffusion-bonded with the material forming the endplate. Steps 902-904 provide for an endplate having a plurality of machined webs, ridges (e.g., ridges 313) or other surface-area increasing features for enhancing bone contact on the bone interface side, and pores on the core interface side for enhancing bonding with the core.

Endplates are shaped from the diffusion bonded assembly if necessary (decision 906), in step 908. Bone interface sides are optionally coated with hydroxyapatite, in step 910, and the endplates are placed in a mold with their core interface layers/sides facing a central cavity, in step 912.

Core material is injection molded between the endplates, and allowed to extrude into the pores (e.g., mesh openings) in the core interface side, in step 914. After setting (Step 916), the interbody device is removed from the mold, in step 918, and endplate and/or core features are created, in optional step 920. Bone interface sides are coated with hydroxyapatite, in step 922, if not already coated, or if additional coating is desired. Steps 906-922 are similar to steps 712-726, described in greater detail above.

Figure 34:
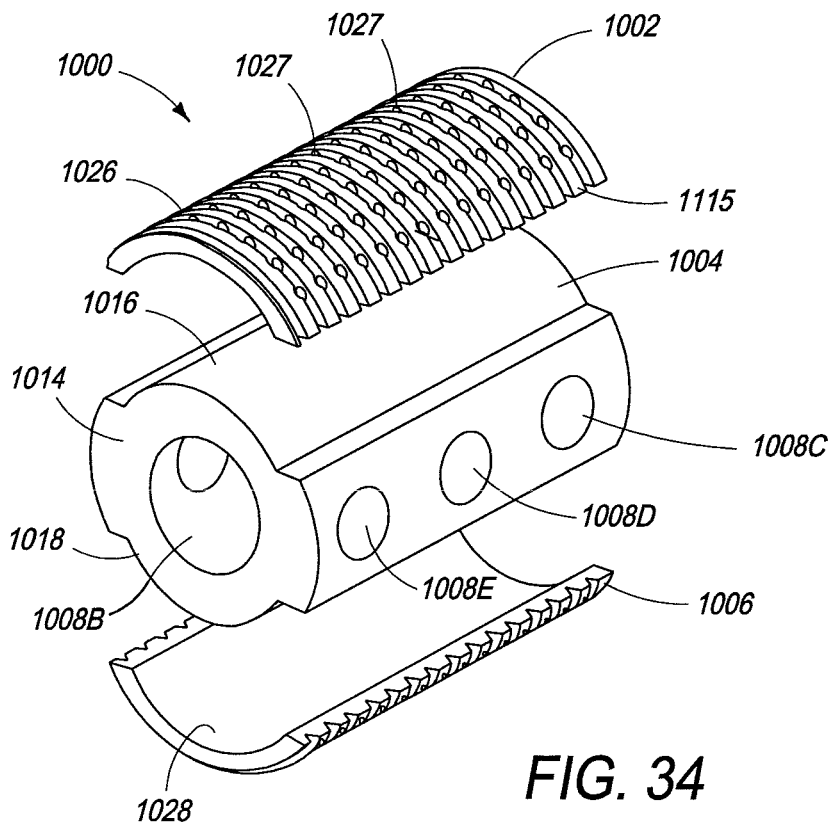
FIG. 34 is a simplified exploded, perspective view of a composite interbody device with superior and inferior endplates, according to an embodiment.
Figure 35:
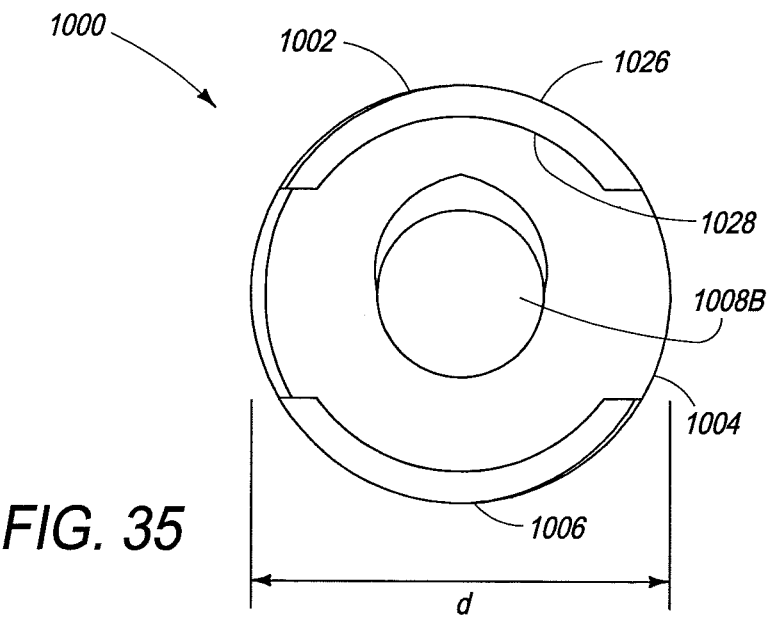
FIG. 35 is an end view of the device of FIG. 34.

FIG. 34 shows a composite interbody device 1000 including a superior endplate 1002 and an inferior endplate 1006, flanking a core 1004. FIG. 35 is a simplified front view of assembled device 1000. FIGS. 36-39 show details of endplate 1002 of device 1000, prior to formation of threading on endplate 1002. FIGS. 34-39 are best viewed together with the following description.

Core 1004 is for example a PEEK core (i.e., injection molded thermosetting PEEK plastic) having one or more features 1008, such as channels through core 1004, for encouraging bone growth therethrough. Because PEEK is radiolucent, core 1004 may include one or more radio markers 1014 for facilitating visualization of core 1004 on x-ray, during or after implantation. Core 1004 may alternately be made of any other biocompatible material that is sufficiently malleable for forming in a desired shape, yet strong enough to meet durability requirements of an intended implant site. Radiomarkers 1014 may not be required where core 1004 is made of a radio-opaque material.

Features 1008 may be machined after core 1004 is injection molded, or features 1008 may be extruded or otherwise formed with core 1004. Feature 1008A is shown with respect to FIG. 40, and described below. Feature 1008B is a horizontally-oriented channel that runs front-to-back through core 104. Features 1008C-1008E are horizontally-oriented, lateral openings into core 1004, or alternately, lateral channels that run through core 1004, generally perpendicular to channel 1008B and intersecting channel 1008B within core 1004. Channel 1008B accommodates an insertion tool, such as a surgical drill, to facilitate placement of device 1000 at an implant site. Channel 1008B may also allow bone growth through device 1000, when device 1000 is implanted (e.g., between vertebrae to enhance spinal fusion, or at a hip socket to enhance hip fusion). For example, bone growing into device 100 via a vertically-oriented slot 1008A through device 1000 (see FIG. 40 and its description, below) may extend through channel 1008B.

Features 1008C-E accommodate fusion-enhancers such as glues, bone graft or other fusion enhancing materials, and/or permit bone growth therethrough. For example, bone growing within channel 1008A may branch into features 1008C-E, where not fully filled with a fusion-enhancer. When implanted between adjacent vertebrae, features 1008B-E run generally perpendicular with a long axis of the spine.

As shown, device 1000 has a cylindrical shape with a relatively consistent diameter. Diameter d of device 1000 is for example about 20 mm. However, it will be appreciated that the diameter of device 1000 may vary from end to end, to facilitate insertion into a desired implant site. For example, where implanted in an intervertebral space, device 1000 may taper from an end 1007 distal to the spinal column, to an insertion end 1005 that is proximal to the spinal column when device 1000 is implanted. Endplates 1002/1006 (and optionally, core 1004, see FIGS. 36-37) are threaded, to facilitate screwing device 1000 into an implant site. For example, device 1000 may be rotationally advanced into a cavity left by a surgical drill, the cavity having a diameter slightly smaller than diameter d. In one aspect, device 1000 is self tapping. As device 1000 is screwed into place, for example into a cavity created between adjacent vertebrae, threads 1015 decorticate bone of the vertebral endplates and provide bleeding bone edges to enhance bone growth onto and into device 1000. Threads 1015 may further allow for controlled widening of a collapsed disk space, to relieve pressure on compressed nerve roots. In addition, threads 1015 increase surface area of bone interface sides 1026 of endplates 1002 and 1006, for enhanced bone-to-device contact and bonding.

In one aspect, endplates 1002/1006 are threaded titanium, coated with hydroxyapatite (HA) to encourage bone on-growth. It will be appreciated that other biocompatible metals such as molybdenum, cobalt-chrome, stainless steels and other biocompatible alloys, may be used in place of or in addition to titanium in forming endplates 1002 and 1006. Pores 1027 penetrate bone interface sides 1026 of endplates 1002 and 1006, providing a plurality of spaces for bone growth into endplates 1002 and 1006. Core interface sides 1028 of endplates 1002 and 1006 are shown as non-porous surfaces, preventing core 1004 material from seeping into pores 1026 during bonding of core 1004 with endplates 1002 and 1006. However, it will be appreciated that an endplate configuration with porous bone interface and core interface sides, with a barrier layer therebetween, may be incorporated into one or both of endplates 1002 and 1006. Such a configuration is described above with respect to endplate assembly 200 (illustrated in FIGS. 19-22).

Core 1004 may be injection molded between endplates 1002 and 1006 in a manner similar to that described above (see, e.g., FIG. 29 and the corresponding description). Endplates 1002 and 1006 may be formed with threads 1015 prior to injection-molding of core 1004 between the endplates. Optionally, endplates 1002 and 1006 are formed as non-threaded, curved metallic sheets with pores 1027 penetrating bone interface sides 1026. See, e.g., FIGS. 36-39, showing a non-threaded superior endplate 1002. In one aspect, threads 1015 and any additional features (such as features 1008 and endplate apertures, shown and described with respect to FIGS. 40, 41 and 43) are machined into device 1000 after injection molding and hardening of core 1004 between endplates 1002 and 1006.

Figure 37:
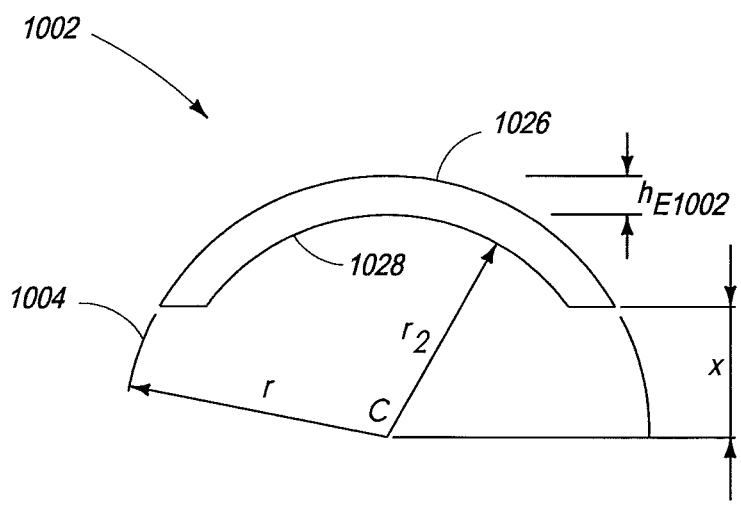
FIG. 37 is an end view of the endplate of FIG. 41.
Figure 38:
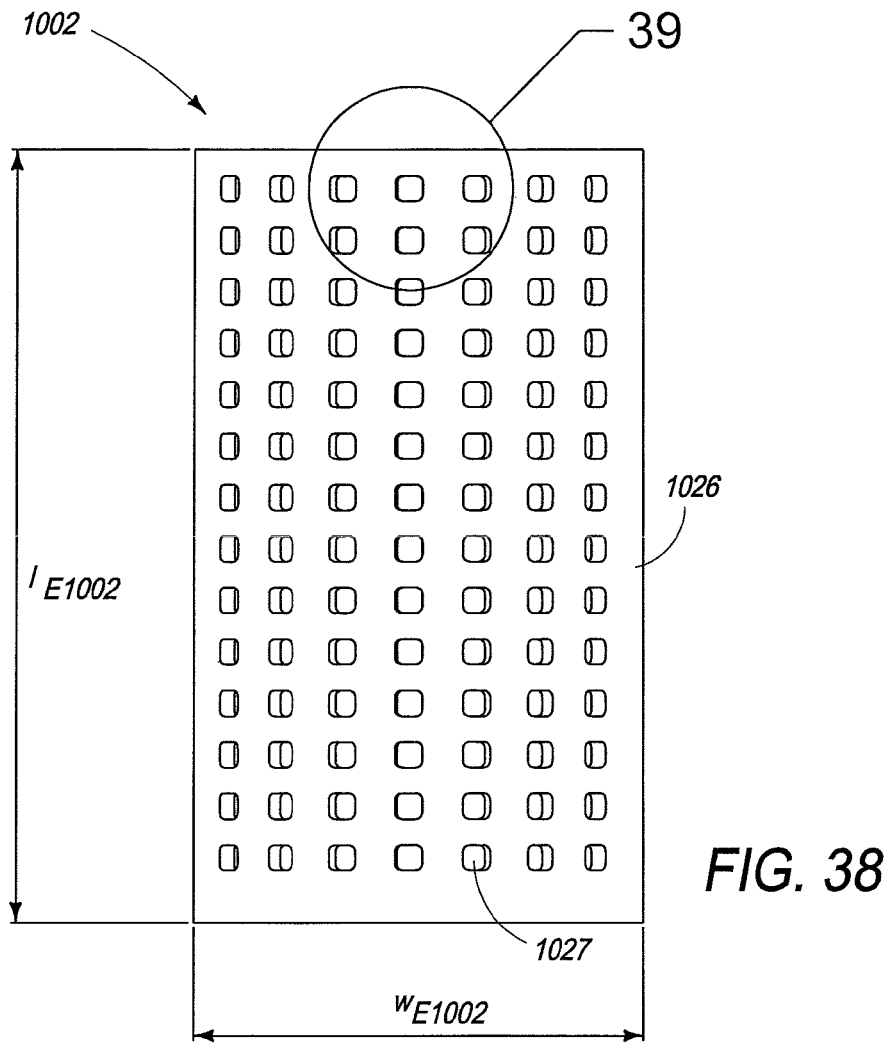
FIG. 38 is a top view of the endplate of FIG. 36.
Figure 39:
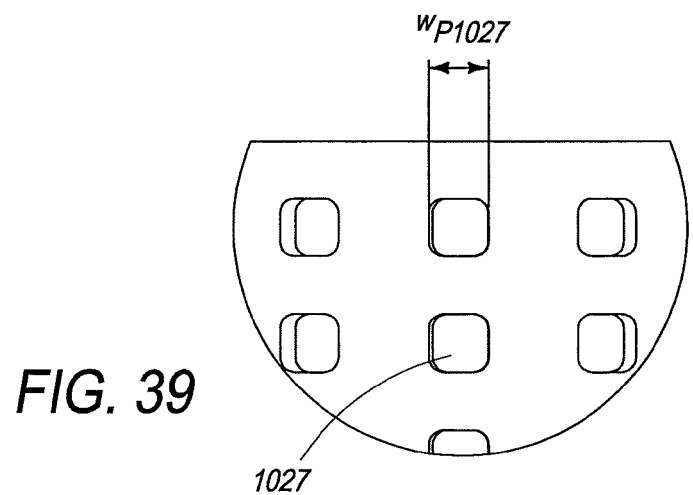
FIG. 39 is an enlarged view of a section of the endplate shown in FIG. 38.

Endplate 1002 has a length ($l_{E1002}$) of about 30 mm and a width ($w_{E1002}$) of about 17-18 mm (see FIG. 38). In one aspect, the length of device 1000 is also about 30 mm. Endplate 1002 spans the length of device 1000. As shown in FIG. 37, the radius (r) of device 1000 is about 10 mm, whereas a distance ($r_2$) from the center (c) of core 1004 to core interface surface 1028 of endplate 1002 is about 8.5 mm. Endplate 1002 thus has an endplate height ($h_{E1002}$) of about 1.5 mm. Bottom edges of endplate 1002 are spaced at a distance x of about 5 mm from center c of core 1004. Pores 1027 have a major dimension (shown as pore width $w_{P1027}$) of about 600 microns. Endplate 1002 and endplate 1006 may be coated with hydroxyapatite before or after assembly with core 1004. In one example, endplates 1002/1006 are formed by diffusion bonding any metallic components (i.e., a sheet forming core interface side 1028, a sheet forming bone interface side 1026 and any barrier layer therebetween) together in a press shaped to produce a desired endplate shape or contour. Formed endplates 1002/1006 are spray coated with hydroxyapatite prior to placement in a mold, and core 1004 is injection molded into a cavity between endplates 1002/1006.

Figure 36:
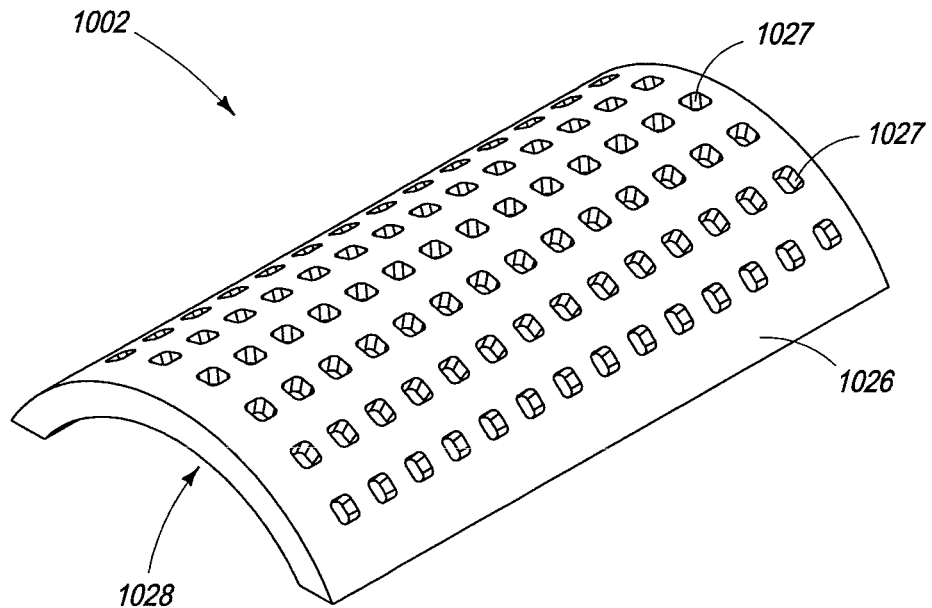
FIG. 36 is a perspective view of the superior endplate of FIG. 39.
Figure 40:
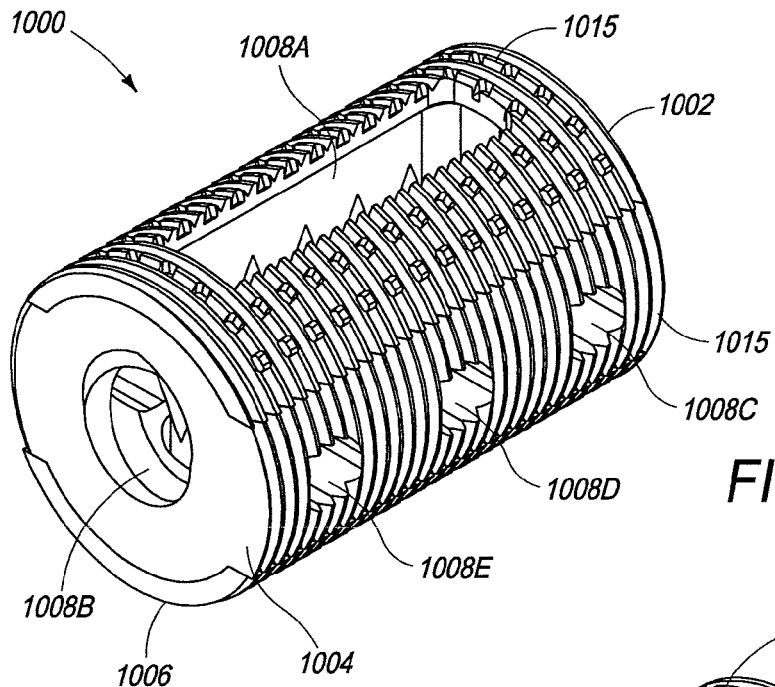
FIG. 40 is perspective view of the assembled device of FIG. 34, including post-assembly, machined features, according to an embodiment.
Figure 41:
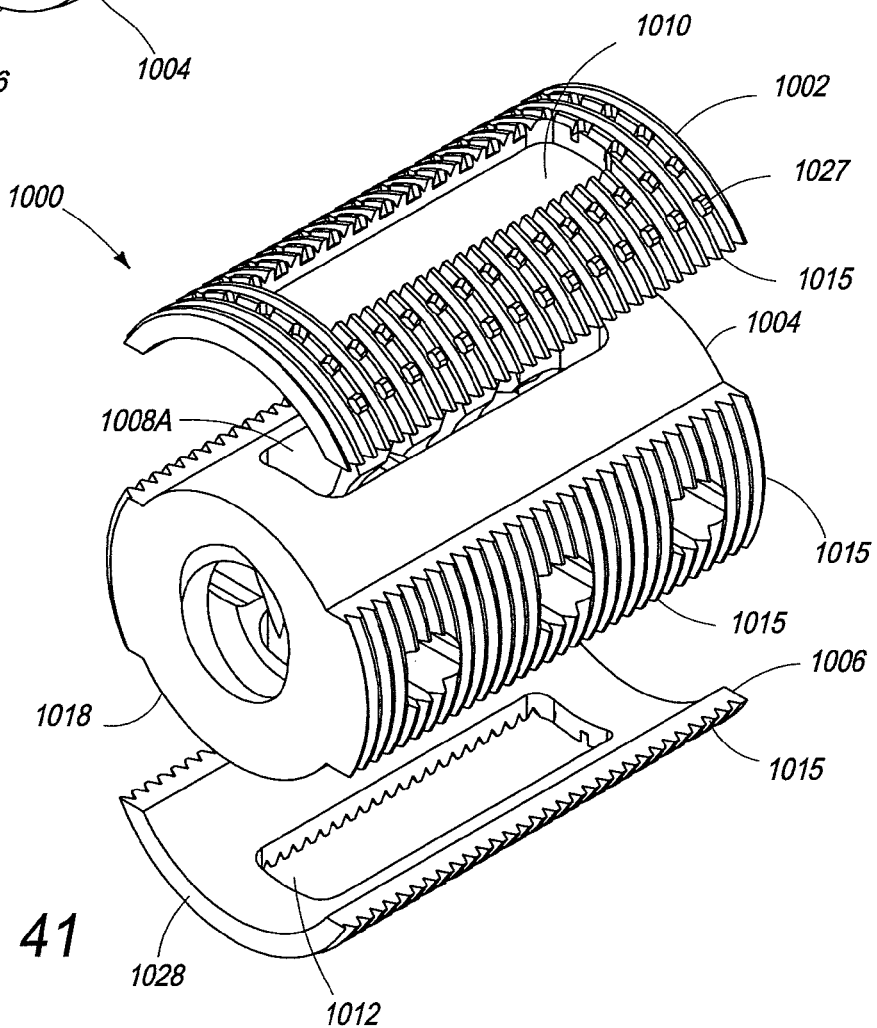
FIG. 41 is an exploded view of the device of FIG. 40.

FIGS. 40-44 show device 1000 with threading 1015 applied to core 1004 and endplates 1002, 1006. FIGS. 40-44 are best viewed together with the following description. In one embodiment, core 1004 is injection-molded between unthreaded superior and inferior endplates 1002 and 1006 (see, e.g., superior endplate 1002 as shown in FIG. 36), and threading 1015 is thereafter machined onto the outer, middle surface of cylindrical device 1000. Thus, as shown in FIGS. 40-44, superior endplate 1002, core 1004 and inferior endplate 1006 all include threading 1015. Threading 1015 may be continuously applied over core 1004 and endplates 1002/1006, as shown in FIG. 40, eliminating the need to align threading 1015 on previously-machined endplates 1002, 1006 with threading of core 1004.

In one aspect, channel 1008A is machined through the diameter of core 1004 and aligns superior and inferior endplate apertures 1010 and 1012, respectively. Channel 1008A is for example a narrow slot that opens into and runs substantially perpendicular to channel 1008B through core 1004, and likewise runs substantially perpendicular to, and may intersect one or more of, lateral channels 1008C-1008E within core 1004. Superior aperture 1010, channel 1008A and inferior aperture 1012 may be machined through superior endplate 1002, core 1004 and inferior endplate 1006 in a single operation to create an opening for bone growth entirely through device 1000. Optionally, endplates 1002 and 1006 are formed with respective apertures 1010 and 1012 prior to placement in a mold, and channel 1008A is formed via molding. Bone growing into device 1000 through channel 1008A (via endplate apertures 1010, 1012) may spread into channel 1008B and portions of channels 1008C-E that are not blocked by fusion enhancing glue.

Endplates 1002 and 1006 are curved to conform to a desired shape (e.g., a cylindrical shape) of core 1004 and to facilitate screw-type insertion at an implant site. Device 1000 length ($l_{D1000}$), shown in FIGS. 42-43, is about 30 mm. Channel 1008A length ($l_{ch}$) and width ($w_{ch}$) are about 22 mm and 6 mm, respectively. Lateral channels 1008C-1008E have a width ($w_{lat}$) and a length ($l_{at}$) of about 4 mm. As previously noted, diameter d of device 1000 may be about 20 mm consistently, or may vary along device 1000, for example if device 1000 tapers from end 1007 to end 1005.

It will be appreciated that although device 1000 is shown and described with one superior and one inferior endplate, device 100 may alternately include a plurality of endplates formed from titanium segments spaced about the perimeter of device 1000, and oriented along the long axis thereof.

FIGS. 45-52 illustrate a generally kidney-shaped composite interbody device 2000 having superior and inferior endplates 2002 and 2006, respectively, on inferior and superior sides of a core 2004. Core 2004 is made of a biocompatible material that is sufficiently malleable for forming in a desired shape, yet strong enough to meet durability requirements of an intended implant site. In one embodiment, core 2004 is for example PEEK plastic that is injected between endplates 2002 and 2006 in a mold, and cooled to harden and bond. Alternately, superior and inferior endplates 2002 and 2006 may be press-fit with core 2004, bonded to core 2004 with a biocompatible adhesive, or mechanically attached to core 2004 using lock-and-key features such as v-grooves, or fasteners such as small screws.

Figure 46:
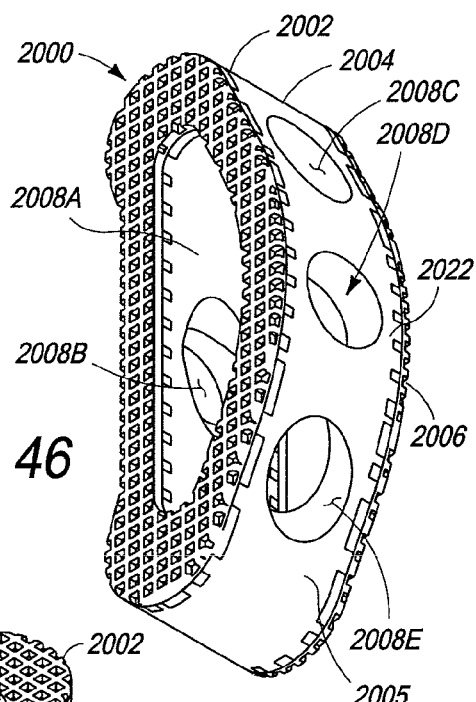
FIG. 46 is a second perspective view of the device of FIG. 45.

On an insertion side 2005, core 2004 curves outward to form a nose portion 2022 (see FIG. 46). Nose portion 2022 may facilitate insertion at an implant site (i.e., between adjacent vertebrae). Core 2004 has one or more features 2008, such as apertures into or channels through core 2004, for encouraging bone through growth. Feature 2008A is a vertically-oriented channel through core 1004. Feature 2008B is an aperture through a back side 2007 of core 2004 (side 2007 is distal to the spinal cord when inserted between vertebrae), which facilitates insertion of device 2000 into an implant site. Aperture 2008B is for example sized to accommodate a selected insertion tool. One or more of features 2008 may optionally be packed with bone and/or other materials to enhance fusion.

Aperture 2008B opens into channel 2008A. Three insertion-side apertures 2008C-20008E through insertion side 2005 also open into channel 2008A. Features 2008C-2008E may be filled partially or completely with fusion-enhancing glue or other fusion aids. Optionally or additionally, features 2008C-E, and/or feature 2008B, facilitate bone growth through core 2004/device 2000. For example, bone growing through vertical channel 2008A through device 2000 may encroach into features 2008B-E from within core 2004, where these features are not fully obstructed by a fusion aid. Features 2008A-D may be machined after core 2004 is molded (e.g., after injection-molding core 2004 between endplates 2002 and 2006), or features 2008A-2008D may be extruded or otherwise formed.

Figure 45:
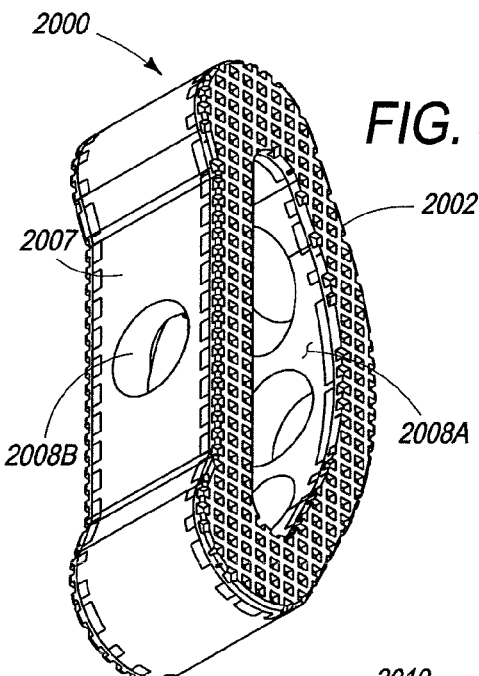
FIG. 45 is a perspective view of a composite interbody device having superior and inferior endplates, according to an embodiment.
Figure 47:
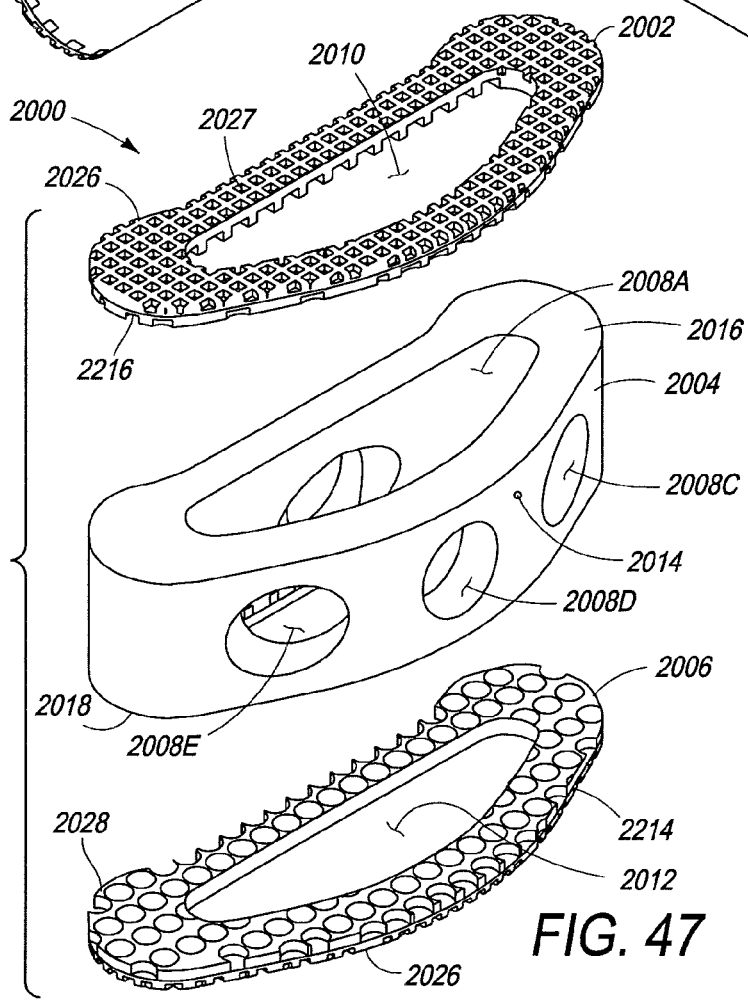
FIG. 47 is an exploded view of the device of FIGS. 45-46.

As illustrated in the exploded view of FIG. 47, channel 2008A aligns with an aperture 2010 in superior endplate 2002 and with an aperture 2012 in inferior endplate 2006 when device 2000 is assembled as shown in FIGS. 45 and 46. Where core 2004 is fanned of radiolucent material, such as PEEK plastic, one or more radio markers 2014 facilitate visualization of core 2004 on x-ray, for example once device 2000 is implanted. Superior endplate 2002 bonds with a superior endplate contact surface 2016 of core 304, and endplate 2006 bonds with an inferior endplate contact surface 2018, as shown in FIG. 47.

As also illustrated in FIG. 47, endplates 2002 and 2006 include a porous bone-interface side 2026 and a porous core interface side 2028, separated by a barrier layer 2216, which is for example similar to barrier layer 216 of endplate assembly 200. Porous metal sheets fanning bone and core interface sides 2026 and 2028 may be diffusion bonded with barrier layer 2216 therebetween, in a press shaped to lend any desired contour to endplate 2002 and/or 2026. Pores 2027 of bone interface side 2026 are smaller than pores 2214 of core interface side 2028. Larger pores 2214 admit molten core 2004 material and facilitate core-to-endplate bonding, while barrier layer 2216 prevents extrusion of core 2004 material into smaller pores 2027, which are reserved for bone in-growth. Pores 2027 may be sized for optimal bone in-growth; for example about 600 microns in diameter or across a major dimension.

Alternately or additionally, as described above with respect to FIG. 25 and device 300, endplates 2002 and 2006 may be machined with geometric features protruding therefrom to increase relative endplate surface area for bone on-growth on bone interface sides 2026. Endplates 2002 and 2006 may be also be formed with ridges similar to ridges 313 of device 300 (see FIGS. 23-27), thin webs or other geometric features, for example features resulting from plate fracture, to increase endplate surface area. Core interface sides 2028 of endplates 2002 and 2006 may also bear geometric features for increasing surface area of core interface sides 2028, to enhance bonding with core 2004 material. It will be appreciated that endplates 2002 and 2004 may alternately be formed by metallic mesh layers separated by a barrier layer (as described above with respect to assembly 200), or by bonding a porous metallic layer with a titanium sheet having ridges or other area-enhancing features on its opposite side (as described above with respect to device 3000).

Figure 48:
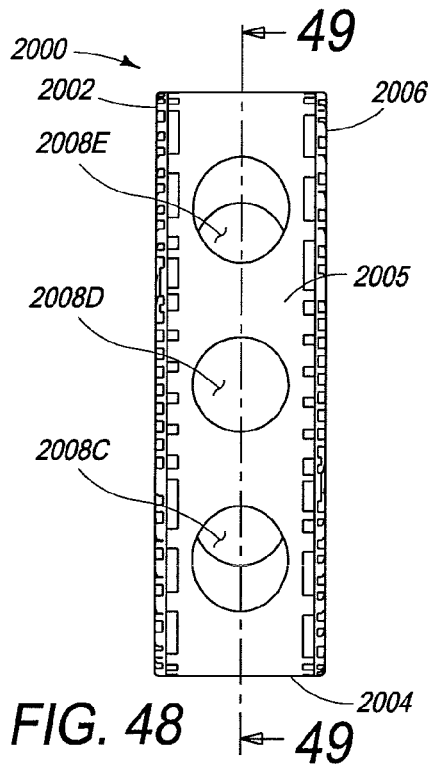
FIG. 48 is a side view of the device of FIGS. 45-47.
Figure 49:
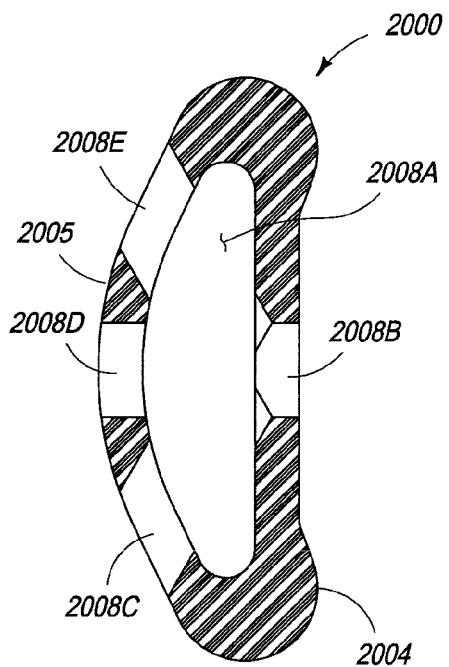
FIG. 49 is a cross-sectional view through the device of FIG. 48.

FIG. 48 is view of device 2000 from insertion side 2005, and FIG. 49 is a cross-sectional view along line 49-49 of FIG. 48. FIGS. 48 and 49 show feature 2008D substantially aligned with feature 2008B, providing a horizontally oriented (when device 2000 is implanted) channel completely through device 2000. Features 2008D and 2008B may be equal in size, as shown, or feature 2008D may be smaller than feature 2008B so that an surgical tool inserted through feature 2008B will not fit completely into feature 2008D. In such a case, feature 2008B provides support for an insertion device while insertion side 2005, proximate feature 2008D, provides resistance necessary to advance device 2000 within an implant site.

Figure 50:
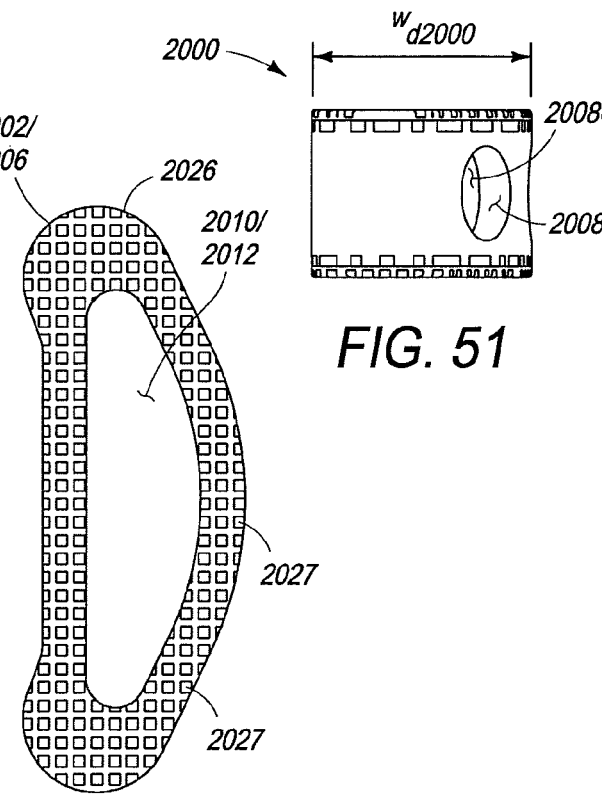
FIG. 50 is a top view of the superior endplate of the device of FIGS. 45-47, showing a bone interface surface.

FIG. 50 is a bone-interface side 2026 view of either superior endplate 2002 or inferior endplate 2006, showing additional detail of bone interface pores 2027. As shown, pores 2027 need not be circular but may instead be square or rectangular (e.g., where formed by a metallic mesh). Other pore geometries are also within the scope hereof.

Figure 51:
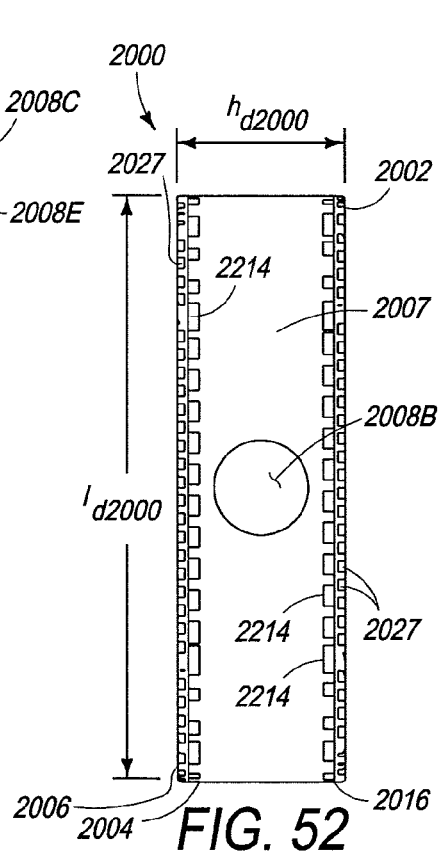
FIG. 51 is an end view of the device of FIGS. 45-47.
Figure 52:
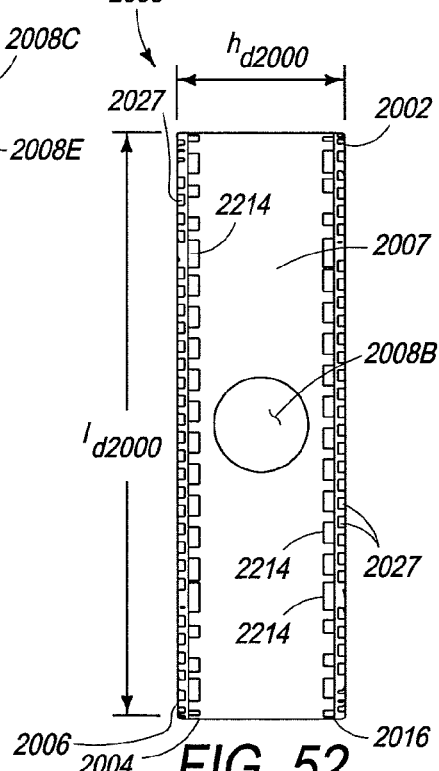
FIG. 52 is a side view of the device of FIGS. 45-47, showing a lateral channel for bone through-growth.

FIG. 51 is an end view of device 2000, showing feature 2008C visible through feature 2008E. Device 2000 width ($w_{D2000}$), shown in FIG. 51 (a rear-side 2007 view of device 2000), may be similar to width $W_D$ of device 100. Device 2000 length ($l_{D2000}$) and height ($h_{D2000}$), shown in FIG. 52, may also be similar to length ($l_D$) and height ($h_D$) of device 100 (see FIGS. 2-3). In one embodiment, $l_{D2000}$ is 20-30 mm and $h_{D2000}$ is about 8-15 mm.

It will be appreciated that device 1000 or device 2000 may be formed according to the methods illustrated in FIGS. 29-33. In one alternate example of method 500 (FIG. 29), inferior and superior endplates 1002 and 1006 are assembled, in step 502, and placed in a mold with core interface sides 1028 facing a core cavity in the mold, in step 504. Core material 1004 is injection molded into the cavity and, through the cavity, into pores of the core interface side, in step 506. Note that while core interface pores are not shown with respect to device 1000, they are within the scope hereof.

The endplate 1002-core 1004-endplate 1006 assembly is allowed to set (for example, the assembly may be cooled until core 1004 fully hardens), in step 508, and removed from the mold, in step 510. One or more of features 1008A-1008E are formed in interbody device 1000, in step 512. In one example of step 512, features 1008A-1008E in core 1004 and apertures 1010 and 1012 through respective endplates 1002 and 1006 are formed in device 1000. For example, one channel may be drilled through device 1000 to form aperture 1010, channel 1008A and aperture 1012 (See FIGS. 40-41). Bone interface surfaces of the device (i.e., bone interface surfaces 1026 of endplates 1002 and 1006) are coated with hydroxyapatite, in step 514. It will be appreciated that although shown as a final step in FIG. 29, hydroxyapatite may alternately or additionally be coated onto bone interface surfaces 1026 prior to their incorporation into endplates 1002 and 1006 (i.e., where endplates 1002 and 1006 are formed in a multi-step process, as with assembly 200, FIG. 19), or after formation of endplates 1002 and 1006 and prior to placement in the mold.

In one alternate example of method 31, metallic wire mesh is selectively layered to form bone interface side 2026, in step 702. For example, one or more sheets of titanium wire mesh is placed or layered to form bone interface side 2026 of endplate 2002 and/or endplate 2006. Central barrier layer 2216 is formed from a solid metallic (e.g., titanium) sheet placed on bone interface side 2026, and core interface side 2028 is formed from larger-weave metallic mesh, placed on central barrier layer 2216, in steps 704 and 706. In one aspect, bone interface side 2026 is formed by selectively placing together titanium wire mesh layers 204 and 206 of assembly 200 (FIG. 19), such that bone interface pores 2027 formed by openings in the mesh are at a desired orientation, one layer relative to the other. As noted above, pores 2214 of core interface side 2028 are larger than pores 2027 of bone interface side 2026, to reduce flow restriction on the core interface side for enhanced core-to-endplate bonding.

Bone interface side 2026, barrier layer 2216 and core interface side 2028 are diffusion bonded together, in step 708. If shaping is required (decision 710), endplates 2002 and 2006 are shaped from the bone interface side/barrier layer/core interface side assembly, in step 712, and optionally coated with hydroxyapatite on bone interface sides 2026, in step 714. Step 714 is illustrated as a dotted box to indicate that hydroxyapatite coating may take place at other points in method 700, for example at position 726 or elsewhere.

Endplates 2002 and 2006 are placed in a mold with bone interface sides 2026 facing a core cavity, in step 716, and core material 2004 is injection molded between the endplates, and allowed to extrude into pores 2027, in step 718. After setting (step 720), interbody device 2000 is removed from the mold, in step 722, and endplate 2002/2006 and/or core 2004 features are created, in optional step 724. For example, after rough interbody device 2000 is removed from the mold, endplate apertures 2010 and 2012 are formed in endplates 2002 and 2006, respectively, if not already formed; and channel 2008A and any of features 2008B-2008E that were not formed in molding are machined into core 2004. For example, apertures 2010, 2012 and channel 2008A are drilled through device 2000.

Bone interface sides 2026 may be coated with hydroxyapatite after device 2000 is machined with its desired features, after endplates 2002 and 2006 are shaped from the bone interface side/barrier layer/core interface side assembly, or both. Alternately, the one or more mesh or perforated layers forming bone interface sides 2026 may be coated with hydroxyapatite prior to placing the layers together to form bone interface sides 2026, or bone interface side 2026 may be coated with hydroxyapatite prior to its placement with central barrier layer 2116. The depth and placement of hydroxyapatite coating may vary as a function of an intended implant site.

While the present invention has been described above, it should be clear that many changes and modifications may be made to the process and product without departing from the spirit and scope of this invention. For example, select or all components of the above-described devices may provide an inter-bone bridge used for bone fusions outside of the spine. Additionally, components of different endplates described above may be combined, without departing from the scope hereof.

What is claimed is:

1. A method for enhancing an interbody device, comprising:
   securing a superior endplate having a porous bone interface surface to a superior surface of a preexisting interbody device, on a side opposite the bone interface surface; and
   securing an inferior endplate having a porous bone interface surface to an inferior surface of the device, on a side opposite the bone interface surface;
   each of the superior and inferior endplates comprising a central barrier layer and a porous device interface surface;
   wherein securing the endplates to the device comprises applying the endplates to the interbody device as a composite coating; and
   wherein securing each endplate to the device comprises applying a bonding agent to one or both of (a) the porous device interface surface and (b) the surface of the interbody device, the central barrier layer preventing diffusion of the bonding agent into the bone interface side.

2. Method of claim 1, wherein applying the endplates as a composite coating comprises (a) applying a solid barrier layer with each of the superior and inferior surfaces of the interbody device, and (b) layering or forming a porous bone interface layer over the solid barrier layer.

3. Method of claim 2 wherein applying the endplates further comprises applying a porous device interface layer to both the superior surface and the inferior surface of the interbody device, prior to applying the solid barrier layer and the bone interface layer.

4. A method for enhancing an interbody device, comprising:
   securing a superior endplate having a porous bone interface surface with a superior surface of a preexisting interbody device, on a side opposite the bone interface surface; and
   securing an inferior endplate having a porous bone interface surface with an inferior surface of the device, on a side opposite the bone interface surface;
   wherein each of the superior and inferior endplates further comprises a central barrier layer and a porous device interface surface;
   wherein securing the endplate to the device comprises applying a bonding agent to one or both of (a) the porous device interface surface and (b) the surface of the interbody device, the central barrier layer preventing diffusion of the bonding agent into the bone interface side; and wherein securing the endplates with the device further comprises one or more of (a) press-fitting the endplates with the device, and (b) mechanically attaching the endplates with the device.

5. Method of claim 4, wherein mechanically attaching comprises aligning and joining lock and key features of the device with complimentary lock and key features of the endplates.

6. Method of claim 1, wherein the bonding agent comprises a molten material.

7. Method of claim 1, wherein the bonding agent comprises a material of the superior and inferior surfaces of the preexisting interbody device, in a molten form.

8. Method of claim 1, the bonding agent being selected from the group of a molten or softened plastic and a biocompatible adhesive.

9. Method of claim 8, the molten or softened plastic comprising PEEK plastic.

10. Method of claim 4, wherein the bonding agent comprises a molten material.

11. Method of claim 4, wherein the bonding agent comprises a material of the superior and inferior surfaces of the preexisting interbody device, in a molten form.

12. Method of claim 4, the bonding agent being selected from the group of a molten or softened plastic and a biocompatible adhesive.

13. Method of claim 12, the molten or softened plastic comprising PEEK plastic.

14. A method for enhancing an interbody device, comprising:

securing a superior endplate having a porous bone interface surface to a superior surface of a preexisting interbody device, on a side opposite the bone interface surface; and securing an inferior endplate having a porous bone interface surface to an inferior surface of the device, on a side opposite the bone interface surface;

wherein securing the endplates to the device comprises applying the endplates to the interbody device as a composite coating by (a) applying a porous device interface layer to both the superior surface and the inferior surface of the interbody device, (b) applying a solid barrier layer over the porous device interface layer, and (c) layering or forming a porous bone interface layer over the solid barrier layer.

* * * * *